United States Patent
Murphy et al.

(10) Patent No.: US 9,782,165 B2
(45) Date of Patent: Oct. 10, 2017

(54) TRANSOSSEOUS ATTACHMENT

(71) Applicant: VentureMD Innovations, LLC, North Logan, UT (US)

(72) Inventors: James Murphy, Newton Square, PA (US); Kwan-Ho Chan, Singapore (SG); T. Wade Fallin, Hyde Park, UT (US); Patrick Michel White, West Chester, PA (US)

(73) Assignee: VentureMD Innovations, LLC, Logan, UT (US)

( * ) Notice: Subject to any disclaimer, the term of this patent is extended or adjusted under 35 U.S.C. 154(b) by 992 days.

(21) Appl. No.: 13/674,849

(22) Filed: Nov. 12, 2012

(65) Prior Publication Data

US 2013/0123840 A1    May 16, 2013

Related U.S. Application Data

(60) Provisional application No. 61/558,933, filed on Nov. 11, 2011, provisional application No. 61/597,066, filed on Feb. 9, 2012.

(51) Int. Cl.
| | | |
|---|---|---|
| *A61B 17/06* | (2006.01) | |
| *A61B 17/04* | (2006.01) | |
| *A61F 2/08* | (2006.01) | |

(52) U.S. Cl.
CPC ...... *A61B 17/0482* (2013.01); *A61B 17/0469* (2013.01); *A61B 17/0485* (2013.01); *A61F 2/0805* (2013.01)

(58) Field of Classification Search
CPC ............ A61B 17/0469; A61B 17/0482; A61B 17/0485; A61B 2017/0472
See application file for complete search history.

(56) References Cited

U.S. PATENT DOCUMENTS

| | | | |
|---|---|---|---|
| 1,583,271 | A | 5/1926 | Biro |
| 1,856,721 | A | 5/1932 | Nagelmann |
| 4,441,497 | A | 4/1984 | Paudler |
| 4,622,960 | A | 11/1986 | Tam |
| 4,672,957 | A | 6/1987 | Hourahane |
| 4,890,615 | A | 1/1990 | Caspari et al. |
| 4,898,156 | A | 2/1990 | Gatturna |
| 5,152,790 | A | 10/1992 | Rosenberg et al. |
| 5,176,682 | A | 1/1993 | Chow |
| 5,250,055 | A | 10/1993 | Moore et al. |
| 5,254,126 | A | 10/1993 | Filipi et al. |

(Continued)

FOREIGN PATENT DOCUMENTS

| | | |
|---|---|---|
| EP | 2070481 A1 | 6/2009 |
| WO | WO2010/132310 A1 | 11/2010 |

(Continued)

OTHER PUBLICATIONS

"Arthrex PassPort Button Cannula" (2011) Arthrex, Inc., 6pgs. www.arthrex.com.

(Continued)

*Primary Examiner* — Gregory Anderson
*Assistant Examiner* — Sarah Simpson

(57) ABSTRACT

Techniques and instruments for surgical transosseous attachment to a bone include a guide able to guide the formation of intersecting bone tunnels and a retriever able to retrieve a suture through the bone tunnels.

15 Claims, 25 Drawing Sheets

(56) References Cited

U.S. PATENT DOCUMENTS

| | | |
|---|---|---|
| 5,342,369 A | 8/1994 | Harryman, II |
| 5,350,380 A | 9/1994 | Goble et al. |
| 5,354,300 A | 10/1994 | Goble et al. |
| 5,417,701 A | 5/1995 | Holmes |
| 5,439,467 A | 8/1995 | Benderev et al. |
| 5,454,823 A | 10/1995 | Richardson et al. |
| 5,464,427 A | 11/1995 | Curtis |
| 5,480,403 A | 1/1996 | Lee |
| 5,486,197 A | 1/1996 | Le |
| 5,544,664 A | 8/1996 | Benderev et al. |
| 5,545,180 A | 8/1996 | Le |
| 5,562,683 A | 10/1996 | Chan |
| 5,562,684 A | 10/1996 | Kammerer |
| 5,562,687 A | 10/1996 | Chan |
| 5,569,306 A | 10/1996 | Thal |
| 5,572,770 A | 11/1996 | Boden |
| 5,575,801 A | 11/1996 | Habermeyer et al. |
| 5,584,839 A | 12/1996 | Gieringer |
| 5,601,562 A | 2/1997 | Wolf et al. |
| 5,624,446 A | 4/1997 | Harryman, II |
| 5,649,963 A | 7/1997 | McDevitt |
| 5,681,333 A * | 10/1997 | Burkhart ............ A61B 17/0469 128/898 |
| 5,683,419 A | 11/1997 | Thal |
| 5,688,284 A | 11/1997 | Chervitz et al. |
| 5,700,266 A | 12/1997 | Harryman, II |
| 5,702,397 A | 12/1997 | Goble et al. |
| 5,709,708 A | 1/1998 | Thal |
| 5,730,747 A | 3/1998 | Ek et al. |
| 5,746,754 A | 5/1998 | Chan |
| 5,755,728 A | 5/1998 | Maki |
| 5,776,151 A | 7/1998 | Chan |
| 5,800,447 A | 9/1998 | Wenstrom, Jr. |
| 5,824,009 A | 10/1998 | Fukuda et al. |
| 5,868,762 A | 2/1999 | Cragg et al. |
| 5,891,150 A | 4/1999 | Chan |
| 5,891,168 A | 4/1999 | Thal |
| 5,895,425 A | 4/1999 | Grafton et al. |
| 5,899,921 A | 5/1999 | Caspari et al. |
| 5,906,624 A | 5/1999 | Wenstrom, Jr. |
| 5,935,129 A | 8/1999 | McDevitt |
| 5,947,982 A | 9/1999 | Duran |
| 5,948,000 A | 9/1999 | Larsen |
| 5,964,783 A | 10/1999 | Grafton et al. |
| 6,024,758 A | 2/2000 | Thal |
| 6,045,574 A | 4/2000 | Thal |
| 6,053,916 A | 4/2000 | Moore |
| 6,099,538 A | 8/2000 | Moses et al. |
| 6,120,511 A | 9/2000 | Chan |
| 6,143,017 A | 11/2000 | Thal |
| 6,156,039 A | 12/2000 | Thal |
| 6,183,479 B1 | 2/2001 | Tormala |
| 6,290,711 B1 | 9/2001 | Caspari |
| 6,368,335 B1 | 4/2002 | Chan |
| 6,387,129 B2 | 5/2002 | Rieser et al. |
| 6,511,487 B1 | 1/2003 | Oren et al. |
| 6,514,274 B1 | 2/2003 | Boucher |
| 6,517,542 B1 | 2/2003 | Papay et al. |
| 6,524,317 B1 | 2/2003 | Ritchart et al. |
| 6,527,795 B1 | 3/2003 | Lizardi |
| 6,544,281 B2 | 4/2003 | ElAttrache et al. |
| 6,599,295 B1 | 7/2003 | Tornier |
| 6,623,524 B2 | 9/2003 | Schmieding |
| 6,629,984 B1 | 10/2003 | Chan |
| 6,638,283 B2 | 10/2003 | Thal |
| 6,641,597 B2 | 11/2003 | Burkhart et al. |
| 6,652,561 B1 | 11/2003 | Tran |
| 6,656,183 B2 | 12/2003 | Colleran et al. |
| 6,666,877 B2 | 12/2003 | Morgan et al. |
| 6,692,516 B2 | 2/2004 | West, Jr. et al. |
| 6,723,107 B1 | 4/2004 | Skiba et al. |
| 6,743,233 B1 | 6/2004 | Baldwin et al. |
| 6,770,076 B2 | 8/2004 | Foerster |
| 6,855,157 B2 | 2/2005 | Foerster |
| 6,932,826 B2 | 8/2005 | Chan |
| 6,955,678 B2 | 10/2005 | Gabriel et al. |
| 6,958,067 B2 | 10/2005 | Whittaker et al. |
| 6,984,237 B2 | 1/2006 | Hatch et al. |
| 6,986,781 B2 | 1/2006 | Smith |
| 6,991,636 B2 | 1/2006 | Rose |
| 6,994,725 B1 | 2/2006 | Goble |
| 7,033,364 B1 | 4/2006 | Walters et al. |
| 7,063,724 B2 | 6/2006 | Re et al. |
| 7,077,863 B2 | 7/2006 | Schmieding et al. |
| 7,108,700 B2 | 9/2006 | Chan |
| 7,112,208 B2 | 9/2006 | Morris et al. |
| 7,175,632 B2 | 2/2007 | Singhatat et al. |
| 7,201,756 B2 | 4/2007 | Ross et al. |
| 7,247,164 B1 | 7/2007 | Ritchart et al. |
| 7,309,337 B2 | 12/2007 | Colleran et al. |
| 7,329,272 B2 | 2/2008 | Burkhart et al. |
| 7,341,592 B1 | 3/2008 | Walters et al. |
| 7,377,926 B2 | 5/2008 | Topper et al. |
| 7,381,212 B2 | 6/2008 | Topper et al. |
| 7,399,302 B2 | 7/2008 | Goble et al. |
| 7,465,308 B2 | 12/2008 | Sikora et al. |
| 7,517,357 B2 | 4/2009 | Abrams |
| 7,527,648 B2 | 5/2009 | May |
| 7,530,999 B2 | 5/2009 | Clark et al. |
| 7,569,059 B2 | 8/2009 | Cerundolo |
| 7,585,305 B2 | 9/2009 | Dreyfuss |
| 7,585,311 B2 | 9/2009 | Green et al. |
| 7,594,917 B2 | 9/2009 | Whittaker et al. |
| 7,608,084 B2 | 10/2009 | Oren et al. |
| 7,625,386 B2 | 12/2009 | Abe et al. |
| 7,655,011 B2 | 2/2010 | Whittaker et al. |
| 7,713,286 B2 | 5/2010 | Singhatat |
| 7,749,237 B2 | 7/2010 | Chan |
| 7,771,411 B2 | 8/2010 | Cerundolo |
| 7,803,173 B2 | 9/2010 | Burkhart et al. |
| 7,833,230 B2 | 11/2010 | Cerundolo |
| 7,833,244 B2 | 11/2010 | Cerundolo |
| 7,837,710 B2 | 11/2010 | Lombardo et al. |
| 7,867,251 B2 | 1/2011 | Colleran et al. |
| 7,875,058 B2 | 1/2011 | Holmes, Jr. |
| 7,879,046 B2 | 2/2011 | Weinert et al. |
| 7,879,048 B2 | 2/2011 | Bain et al. |
| 7,883,519 B2 | 2/2011 | Oren et al. |
| 7,887,564 B2 | 2/2011 | Boehringer et al. |
| 7,931,657 B2 | 4/2011 | Walters et al. |
| 7,938,847 B2 | 5/2011 | Fanton et al. |
| 7,942,914 B2 | 5/2011 | Cerundolo |
| 7,955,341 B2 | 6/2011 | Cerundolo |
| 7,963,972 B2 | 6/2011 | Foerster et al. |
| 7,976,565 B1 | 7/2011 | Meridew |
| 7,981,140 B2 | 7/2011 | Burkhart et al. |
| 7,988,697 B2 | 8/2011 | Miller et al. |
| 7,993,369 B2 | 8/2011 | Dreyfuss |
| 8,038,652 B2 | 10/2011 | Morrison et al. |
| 8,043,308 B2 | 10/2011 | Bittenson |
| 8,062,295 B2 | 11/2011 | McDevitt |
| 8,100,942 B1 | 1/2012 | Green et al. |
| 8,105,343 B2 | 1/2012 | White et al. |
| 8,109,966 B2 | 2/2012 | Ritchart et al. |
| 8,109,969 B1 | 2/2012 | Green et al. |
| 8,137,360 B2 | 3/2012 | Whittaker et al. |
| 8,137,381 B2 | 3/2012 | Foerster |
| 8,147,505 B2 | 4/2012 | Delli-Santi |
| 8,177,796 B2 | 5/2012 | Akyuz et al. |
| 8,202,295 B2 | 6/2012 | Kaplan |
| 8,202,297 B2 | 6/2012 | Burkhart |
| 8,231,653 B2 | 7/2012 | Dreyfuss |
| 8,262,675 B2 | 9/2012 | Cropper |
| 8,267,964 B2 | 9/2012 | Green et al. |
| 8,282,643 B2 | 10/2012 | Dross |
| 8,317,829 B2 | 11/2012 | Foerster |
| 8,317,862 B2 | 11/2012 | Troger |
| 8,409,225 B2 | 4/2013 | Bull |
| 8,444,674 B2 | 5/2013 | Kaplan |
| 8,491,595 B2 | 7/2013 | Volpi |
| 8,506,596 B2 | 8/2013 | Stone |
| 8,518,091 B2 | 8/2013 | McDevitt |

(56) References Cited

U.S. PATENT DOCUMENTS

| | | |
|---|---|---|
| 8,540,737 B2 | 9/2013 | Chudik |
| 8,597,328 B2 | 12/2013 | Cauldwell |
| 8,663,280 B2 | 3/2014 | Kaplan |
| 8,740,913 B2 | 6/2014 | Schneider |
| 8,747,469 B2 | 6/2014 | Wang |
| 8,790,370 B2 | 7/2014 | Spenciner |
| 8,808,326 B2 | 8/2014 | Gagliano |
| 8,961,576 B2 | 2/2015 | Hodge |
| 8,986,347 B2 | 3/2015 | Housman |
| 9,011,466 B2 | 4/2015 | Adams et al. |
| 9,023,083 B2 | 5/2015 | Foerster |
| 9,034,014 B2 | 5/2015 | Catania |
| 9,149,268 B2 | 10/2015 | Graul |
| 2001/0016747 A1 | 8/2001 | Romano et al. |
| 2001/0037119 A1 | 11/2001 | Schmieding |
| 2001/0049529 A1 | 12/2001 | Cachia et al. |
| 2001/0049536 A1 | 12/2001 | Chan et al. |
| 2002/0111653 A1 | 8/2002 | Foerster |
| 2002/0147456 A1 | 10/2002 | Diduch et al. |
| 2002/0165546 A1 | 11/2002 | Goble et al. |
| 2003/0078599 A1* | 4/2003 | O'Quinn ............ A61B 17/0469 606/144 |
| 2003/0195528 A1 | 10/2003 | Ritchart |
| 2003/0195563 A1 | 10/2003 | Foerster |
| 2003/0229362 A1 | 12/2003 | Chan et al. |
| 2004/0098051 A1 | 5/2004 | Fallin |
| 2004/0116843 A1 | 6/2004 | Chan |
| 2004/0133239 A1 | 7/2004 | Singhatat |
| 2004/0172062 A1 | 9/2004 | Burkhart |
| 2004/0193172 A1 | 9/2004 | Ross et al. |
| 2004/0193187 A1 | 9/2004 | Boehringer et al. |
| 2004/0267317 A1 | 12/2004 | Higgins |
| 2005/0055052 A1 | 3/2005 | Lombardo et al. |
| 2005/0075668 A1 | 4/2005 | Lizardi |
| 2005/0245932 A1 | 11/2005 | Fanton et al. |
| 2005/0277986 A1 | 12/2005 | Foerster et al. |
| 2005/0283156 A1 | 12/2005 | Schmieding et al. |
| 2006/0004410 A1 | 1/2006 | Nobis et al. |
| 2006/0074438 A1 | 4/2006 | Chan |
| 2006/0079904 A1 | 4/2006 | Thal |
| 2006/0106422 A1 | 5/2006 | Del Rio et al. |
| 2006/0149258 A1 | 7/2006 | Sousa |
| 2006/0235413 A1 | 10/2006 | Denham et al. |
| 2006/0241658 A1 | 10/2006 | Cerundolo |
| 2006/0247642 A1 | 11/2006 | Stone et al. |
| 2006/0276841 A1 | 12/2006 | Barbieri et al. |
| 2007/0088362 A1 | 4/2007 | Bonutti |
| 2007/0112352 A1 | 5/2007 | Sorensen et al. |
| 2007/0123887 A1 | 5/2007 | Hirt et al. |
| 2007/0173865 A1 | 7/2007 | Oren et al. |
| 2007/0179510 A1 | 8/2007 | Stone |
| 2007/0191849 A1 | 8/2007 | ElAttrache et al. |
| 2007/0203498 A1 | 8/2007 | Gerber et al. |
| 2007/0219558 A1 | 9/2007 | Deutsch |
| 2007/0260259 A1 | 11/2007 | Fanton et al. |
| 2007/0270854 A1 | 11/2007 | Li et al. |
| 2008/0004659 A1 | 1/2008 | Burkhart et al. |
| 2008/0009904 A1 | 1/2008 | Bourque et al. |
| 2008/0033486 A1 | 2/2008 | Whittaker et al. |
| 2008/0077161 A1 | 3/2008 | Kaplan |
| 2008/0125815 A1 | 5/2008 | Heaven |
| 2008/0154314 A1 | 6/2008 | McDevitt |
| 2008/0208253 A1 | 8/2008 | Dreyfuss et al. |
| 2008/0262544 A1 | 10/2008 | Burkhart et al. |
| 2008/0275453 A1 | 11/2008 | Lafosse et al. |
| 2008/0287992 A1 | 11/2008 | Tornier |
| 2008/0300629 A1 | 12/2008 | Surti |
| 2009/0018581 A1 | 1/2009 | Anderson |
| 2009/0036905 A1 | 2/2009 | Schmieding |
| 2009/0062819 A1 | 3/2009 | Burkhart et al. |
| 2009/0076544 A1 | 3/2009 | DiMatteo |
| 2009/0088708 A1 | 4/2009 | Boehringer et al. |
| 2009/0099598 A1 | 4/2009 | McDevitt |
| 2009/0112270 A1 | 4/2009 | Lunn et al. |
| 2009/0157124 A1 | 6/2009 | Ferragamo et al. |
| 2009/0187216 A1 | 7/2009 | Schmieding et al. |
| 2009/0192546 A1 | 7/2009 | Schmieding et al. |
| 2009/0234387 A1 | 9/2009 | Miller et al. |
| 2009/0292313 A1 | 11/2009 | Anspach, III |
| 2009/0292321 A1 | 11/2009 | Collette |
| 2009/0312794 A1 | 12/2009 | Nason |
| 2009/0318959 A1 | 12/2009 | Burkhart et al. |
| 2009/0318960 A1 | 12/2009 | Burkhart |
| 2009/0326579 A1 | 12/2009 | Anderhub et al. |
| 2010/0063542 A1 | 3/2010 | Van Der Burg et al. |
| 2010/0069974 A1 | 3/2010 | Oren et al. |
| 2010/0094355 A1 | 4/2010 | Trenhaile |
| 2010/0100127 A1 | 4/2010 | Trenhaile |
| 2010/0114123 A1 | 5/2010 | Nason |
| 2010/0121337 A1 | 5/2010 | Pandya |
| 2010/0121338 A1 | 5/2010 | Pandya |
| 2010/0121348 A1 | 5/2010 | Van Der Burg et al. |
| 2010/0121349 A1 | 5/2010 | Meier et al. |
| 2010/0121354 A1 | 5/2010 | Pandya |
| 2010/0121375 A1 | 5/2010 | Pandya |
| 2010/0137889 A1 | 6/2010 | Oren et al. |
| 2010/0160962 A1 | 6/2010 | Dreyfuss et al. |
| 2010/0179592 A1 | 7/2010 | Martinek et al. |
| 2010/0198235 A1 | 8/2010 | Pierce et al. |
| 2010/0198258 A1 | 8/2010 | Heaven et al. |
| 2010/0228254 A1 | 9/2010 | Pandya |
| 2010/0249806 A1 | 9/2010 | Oren et al. |
| 2010/0249834 A1 | 9/2010 | Oren et al. |
| 2010/0292733 A1 | 11/2010 | Hendricksen et al. |
| 2010/0312249 A1* | 12/2010 | Sanders ............ A61B 17/1684 606/96 |
| 2010/0318139 A1 | 12/2010 | Beauchamp |
| 2010/0324575 A1 | 12/2010 | Chan |
| 2010/0331881 A1 | 12/2010 | Hart |
| 2011/0009867 A1* | 1/2011 | Oren ................ A61B 17/0482 606/80 |
| 2011/0009884 A1 | 1/2011 | Kaplan |
| 2011/0022087 A1 | 1/2011 | Cerundolo |
| 2011/0087245 A1 | 4/2011 | Weinert et al. |
| 2011/0106124 A1 | 5/2011 | Beauchamp |
| 2011/0112550 A1 | 5/2011 | Heaven |
| 2011/0112576 A1 | 5/2011 | Nguyen et al. |
| 2011/0118757 A1 | 5/2011 | Pierce |
| 2011/0118762 A1 | 5/2011 | Dooney, Jr. |
| 2011/0152928 A1 | 6/2011 | Colleran et al. |
| 2011/0208198 A1 | 8/2011 | Anderson |
| 2011/0224726 A1 | 9/2011 | Lombardo |
| 2011/0264140 A1 | 10/2011 | Lizardi et al. |
| 2012/0053626 A1 | 3/2012 | Koepke |
| 2012/0143224 A1 | 6/2012 | Chan |
| 2012/0179199 A1 | 7/2012 | Hernandez et al. |
| 2012/0209279 A1 | 8/2012 | Snyder |
| 2012/0245634 A1 | 9/2012 | Kaplan |
| 2013/0096611 A1 | 4/2013 | Sullivan |
| 2013/0103083 A1 | 4/2013 | Baird |
| 2013/0123809 A1 | 5/2013 | Murphy et al. |
| 2013/0123842 A1 | 5/2013 | Chan et al. |
| 2013/0123843 A1 | 5/2013 | Chan et al. |
| 2013/0144335 A1 | 6/2013 | Sandow |
| 2013/0190871 A1 | 7/2013 | Markarian |
| 2013/0197575 A1 | 8/2013 | Karapetian |
| 2013/0197577 A1 | 8/2013 | Wolf |
| 2013/0197578 A1 | 8/2013 | Gregoire |
| 2013/0204299 A1 | 8/2013 | Mantovani et al. |
| 2013/0345711 A1 | 12/2013 | Mehta |
| 2014/0046369 A1 | 2/2014 | Heaven |
| 2014/0114411 A1 | 4/2014 | Baird |
| 2014/0134802 A1 | 5/2014 | Lin |
| 2014/0172016 A1 | 6/2014 | Housman |
| 2014/0303625 A1 | 10/2014 | Sholev |
| 2014/0343605 A1 | 11/2014 | Lunn |
| 2014/0364905 A1 | 12/2014 | Lunn |

(56) References Cited

U.S. PATENT DOCUMENTS

| | | |
|---|---|---|
| 2015/0119937 A1 | 4/2015 | Lunn |
| 2015/0150551 A1 | 6/2015 | Paulk |
| 2015/0196388 A1 | 7/2015 | Housman |

FOREIGN PATENT DOCUMENTS

| | | |
|---|---|---|
| WO | WO 2011/008607 A1 | 1/2011 |
| WO | WO 2012/007941 A2 | 1/2012 |
| WO | WO 2013/027209 A1 | 2/2013 |
| WO | WO 2013/027210 A1 | 2/2013 |

OTHER PUBLICATIONS

"Arthroscopic Shoulder Repair Using the Smith & Nephew FOOTPRINT PK Suture Anchor" (2008) Smith & Nephew, Inc., 12pgs.
"CurvTek Bone Tunneling System" (2000) Arthrotek, Inc., 6pgs.
"The OPUS® AutoCuff® System Featuring SpeeScrewTM for Rotator Cuff Repair" (2009) Arthrocare Corporation, 8pgs.
ArthroCare Sports Medicine International, Products: SpeedStitch MagnumWire Suture Cartridges, (3ea: white & co-braid), http://www.arthrocaresportsmedicine.com/products/view/435 Sep. 24, 2012, 1pg.
ArthroCare Sports Medicine International, Products: SpeedStitch Suturing Device, http://www.arthrocaresportsmedicine.com/products/view/431 Sep. 24, 2012, 1pg.
Baums, et al. "Tendon-bone contact pressure and biomechanical evaluation of a modified suture-bridge technique for rotator cuff repair" Knee Surg Sports Traumatol Arthrosc (2010) 18:992-998.
Dermirhan, et al. "Current Concept: Arthroscopic Transosseous Equivalent Suture Bridge Rotator Cuff Repair" (2012) 109-115, Springer-Verlag Berlin Heidelberg.
Lorbach and Tompkings "Rotator Cuff: Biology and Current Arthroscopic Techniques" Knee Surg Sports Traumatol Arthrosc, Springer-Verlag, published online: Jan. 21, 2012, 9pgs.
Maguire, et al. "Biomechanical Evaluation of Four Different Transosseous-equivalent/suture Bridge Rotator Cuff Repairs" Knee Surg Sports Traumatol Arhtrosc (2011) 19:1582-1587.
Park, et al. "Part I: Footprint Contact Characteristics for a Transosseous-equivalent Rotator Cuff Repair Technique Compared with a Double-row Repair Technique" J.Shoulder Elbow Surg (2007) 16(4):461-468.
Upper Limb Surgery Info., Adelaide—Wakefield Orthopaedic Clinic, SA, Jan. 30, 2012, 4pgs. http://www.woc.com.au/upper-limb-research.html.
VERSALOKTM The Next Generation in Rotator Cuff Repair, (2007) DePuy Mitek, Inc., www.depuymitek.com, 18pgs.
Multifix's PEEK 5.5mm and 6.5mm Knotless Implants Technique Guide, ArthroCare Corporation, www.smith-nephew.com, Jul. 2015, 8 pp.
Multifix PEEK Knotless Fixation Implants, ArthroCare Corporation, www.smith-nephew.com, Aug. 2015, 6 pp.
Achilles Speedbridge Surgical Technique, Arthrex, Inc., www.arthrex.com, 2013, 6 pp.
Achilles Suturebridge Surgical Technique, Arthrex, Inc., www.arthrex.com, 2014, 6 pp.
Massive Rotator Cuff Repair and Augmentation using the Speedbridge and ArthroFlex Dermal Matrix Surgical Technique, Arthrex, Inc., www.arthrex.com, 2012 4 pp.
Arthrex is Reaching New Heights in Rotator Cuff Repair, Arthrex, Inc. www.arthrex.com, 2007, 8 pp.
Speedbridge and SpeedFix Knotless Rotator Cuff Repair using the SwiveLock C and FiberTape Surgical Technique, Arthrex, Inc. www.arthrex.com, 2013, 8 pp.
SutureBridge Double Row Rotator Cuff Repair Surgical Technique, Arthrex, Inc. www.arthrex.com, 2013, 6 pp.
Duattro Shoulder System—Innovative Rotator Cuff Solutions, Cayenne Medical, Inc., www.cayennemedical.com, 6 pp.
Shoulder Restoration System—PopLok Knotless Suture Anchor Surgical Technique, ConMed Linvatec, www.linvatec.com, 2013, 8 pp.
The Next Generation in Rotator Cuff Repair, DePuy Mitek, Inc., www.depuymitek.com, 2007, 18 pp.
Footprint PK Suture Anchor, Arthroscopic Shoulder Repair Using the Smith & Nephew Footprint PK Suture Anchor Technique Guide, Smith & Nephew, Inc., www.smith-nephew.com, Apr. 2008, 12 pp.
Mall, Nathan A., et al. "Transosseous-Equivalent Rotator Cuff Repair: A Systematic Review on the Biomechanical Importance of Tying the Medial Row", The Journal of Arthroscopic and Related Surgery, vol. 29, No. 2, Feb. 2013, pp. 377-386.
Sharc-FT and Taylor Stitcher Transosseus Devices for Fast Rotator Cuff Repair Surgical Technique, NCS Lab Medical Devices Factory, 12 pp.
Comprehensive Product Offerings for Your Rotator Cuff Repair, Smith&Nephew, Inc., www.smith-nephew.com, Jul. 2015, 12 pp.
OPUS AutoCuff, Magnum X Knotless Fixation Implant with Independent Tensioning, ArthroCare Sports Medicine, arthrocaresportsmedicine.com, 2009, 2 pp.
The OPUS TwinLock Knotless Fixation System, ArthroCare Sports Medicine, arthrocaresportsmedicine.com, 2010, 2 pp.
The OPUS AutoCuff System for Rotator Cuff Repair, ArthroCare Sports Medicine, arthrocaresportsmedicine.com, 2006, 8 pp.
BioRaptor—Knotless Suture Anchor, Smith&Nephew, Inc., www.smith-nephew.com, Apr. 2010, 6 pp.
Footprint PK Arthroscopic Shoulder Repair Using the Smith&Nephew Footprint PK Suture Anchor Technique Guide, Smith&Nephew, Inc., www.smith-nephew.com, Apr. 2008, 12 pp.
CinchLock SS (Sports Sheath) Knotless Labrum Restoration Surgical Technique, Pivot Medical, Inc., 6 pp.
ReelX STT Knotless Anchor System, Stryker, www.stryker.com, 2010, 4 pp.
Dr. S.D. Gerber Double Row Method Surgical Technique, Stryker, www.stryker.com, 2010, 12 pp.
ArthroTunneler TunnelPro System Transosseous Rotator Cuff Repair, Tornier, Inc., www.tornier.com, 2012, 6 pp.
Quickdraw Knotless Suture Anchor System Surgical Technique, ArthroCare Corporation, www.arthrocare.com, 2011, 28 pp.
European Search Report for EP 12846903.8, dated Jun. 25, 2015, 7 pp.
International Search Report and Written Opinion for PCT/US2012/064669, dated Nov. 12, 2012; 14 pp.

* cited by examiner

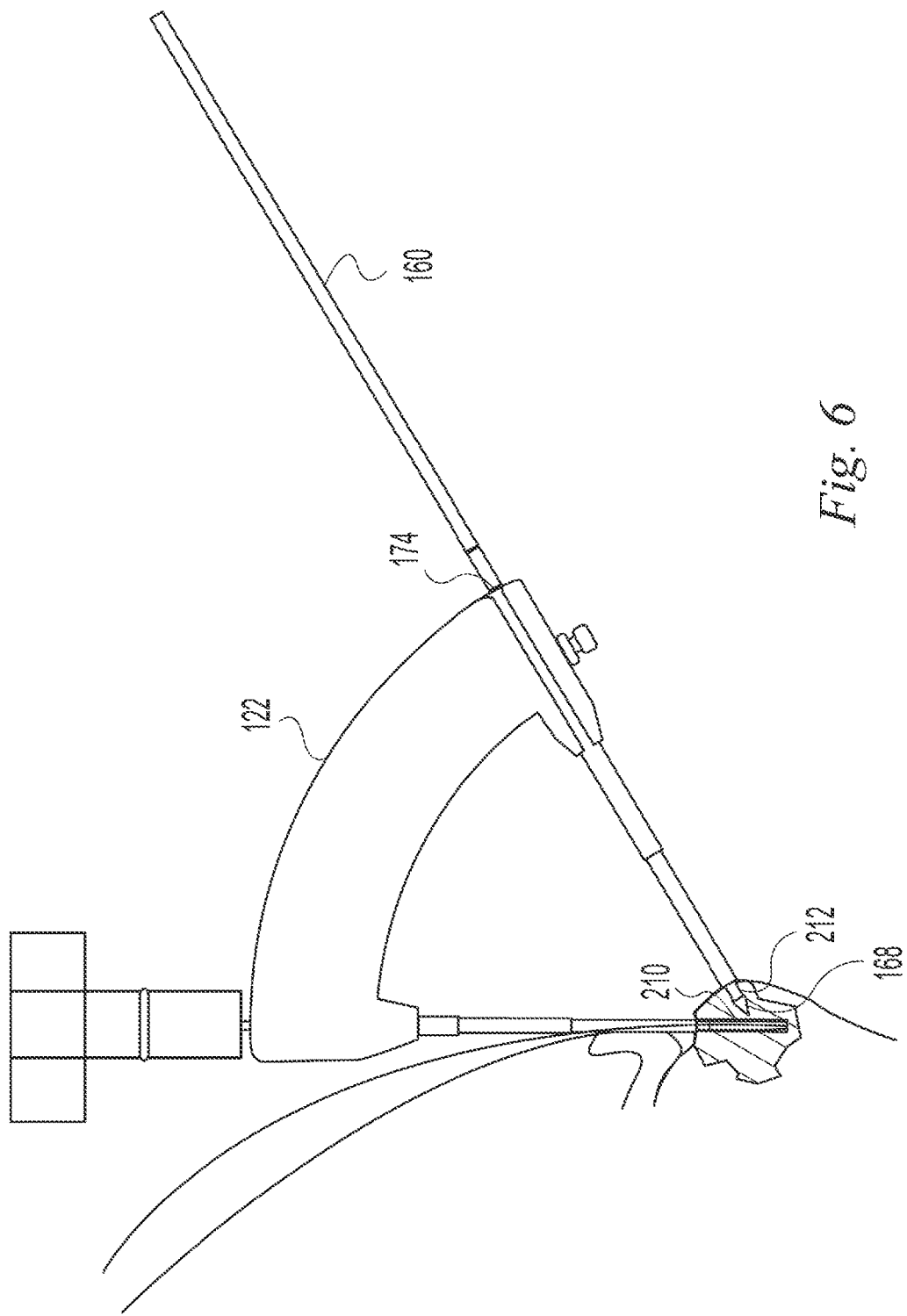

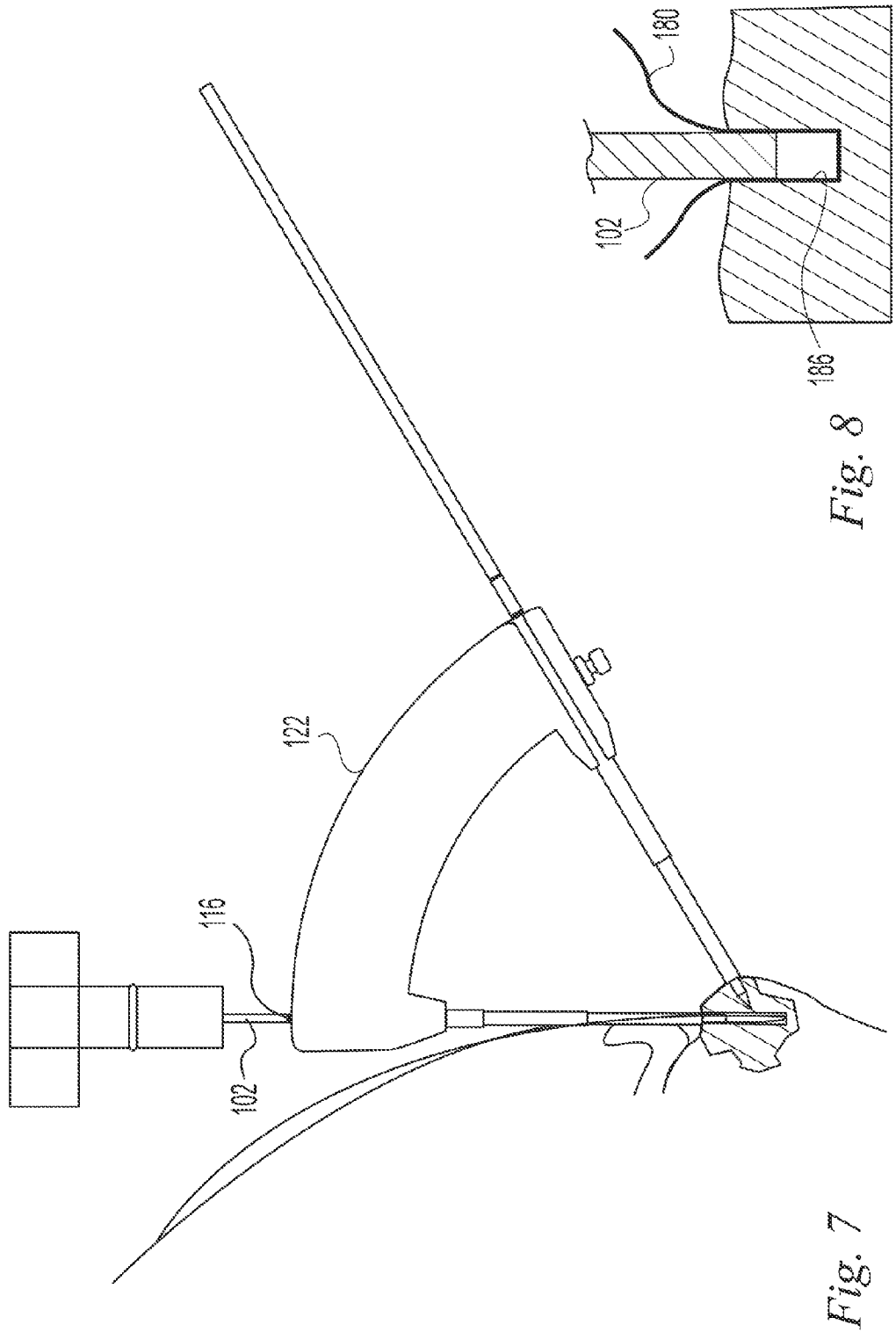

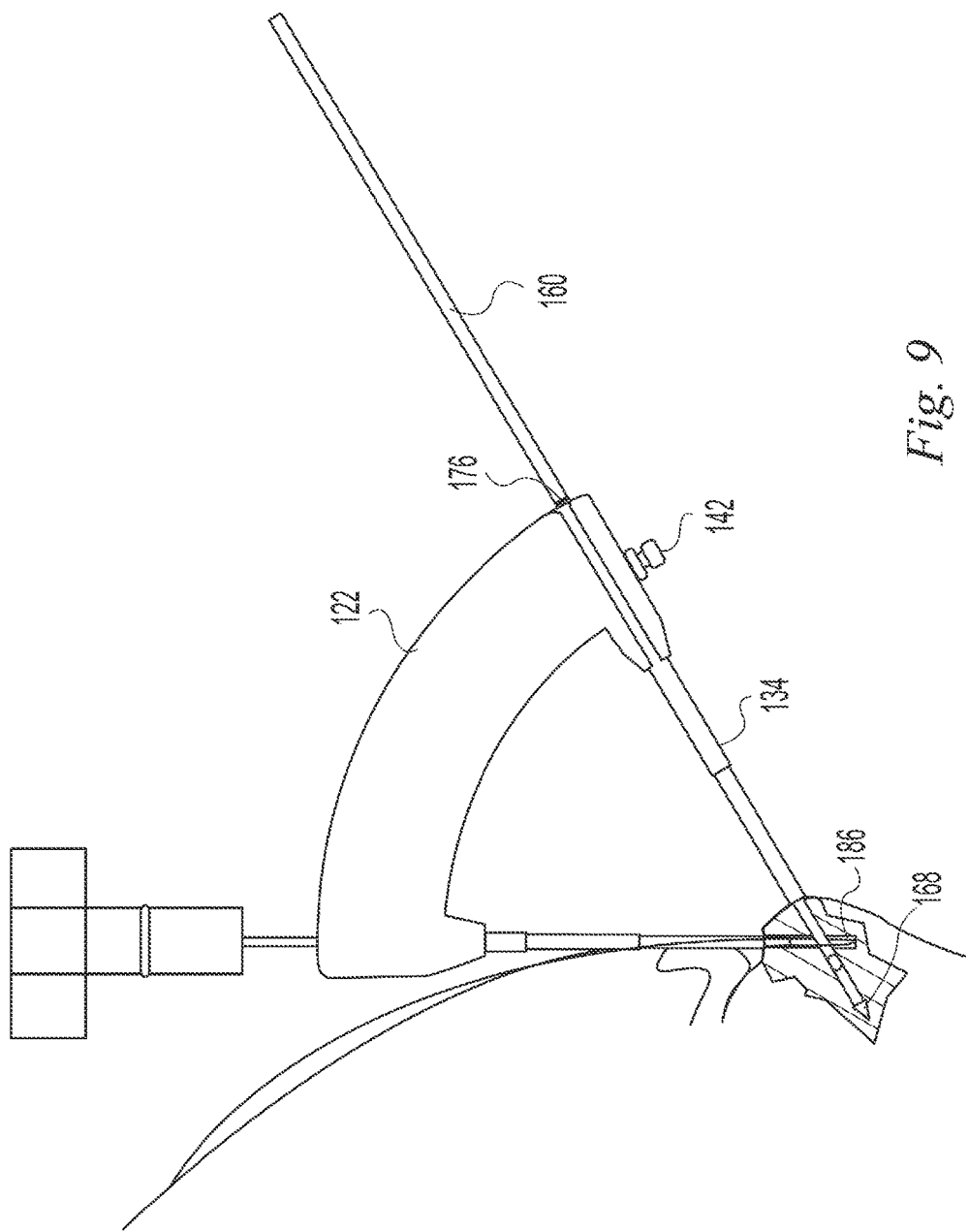

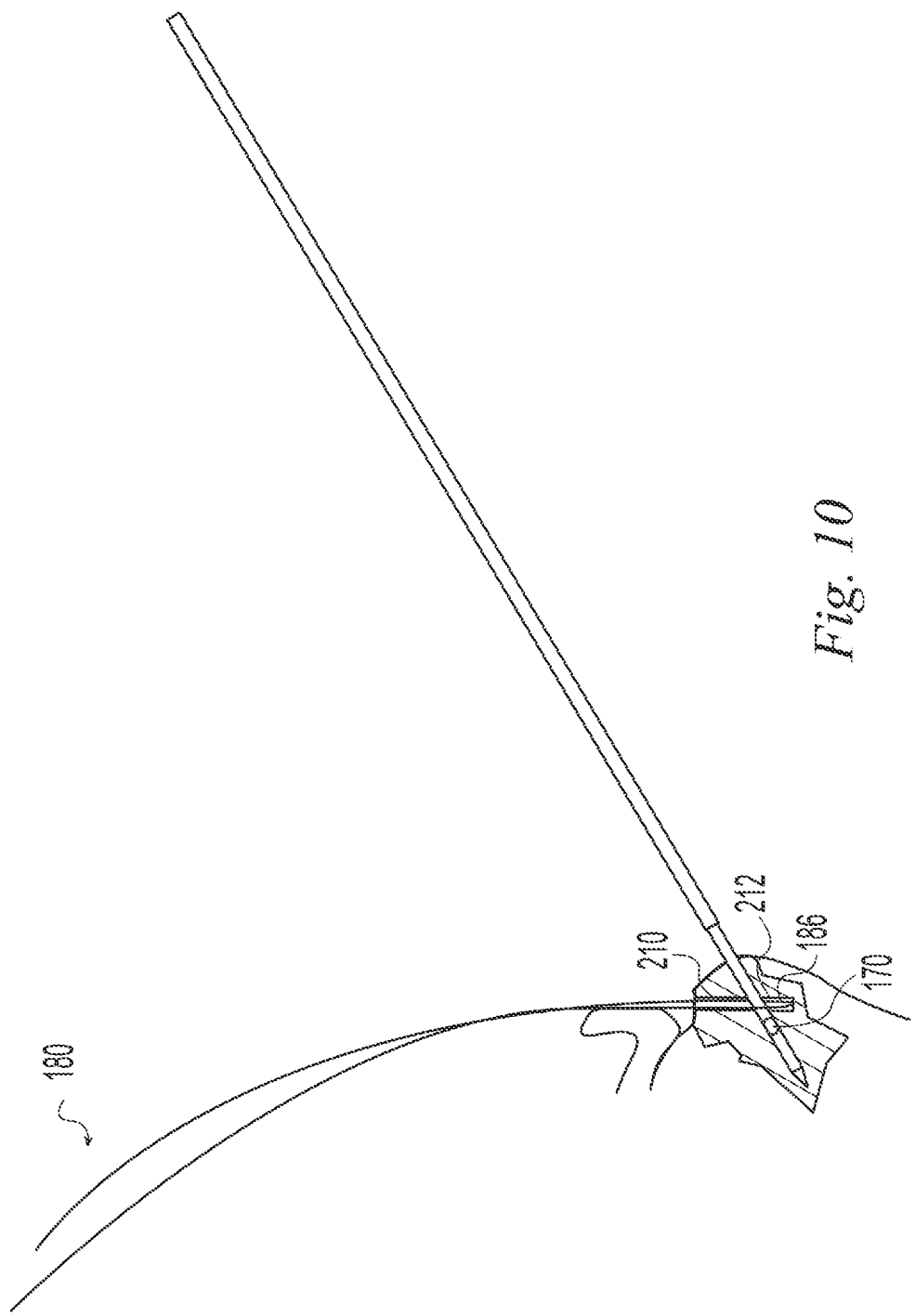

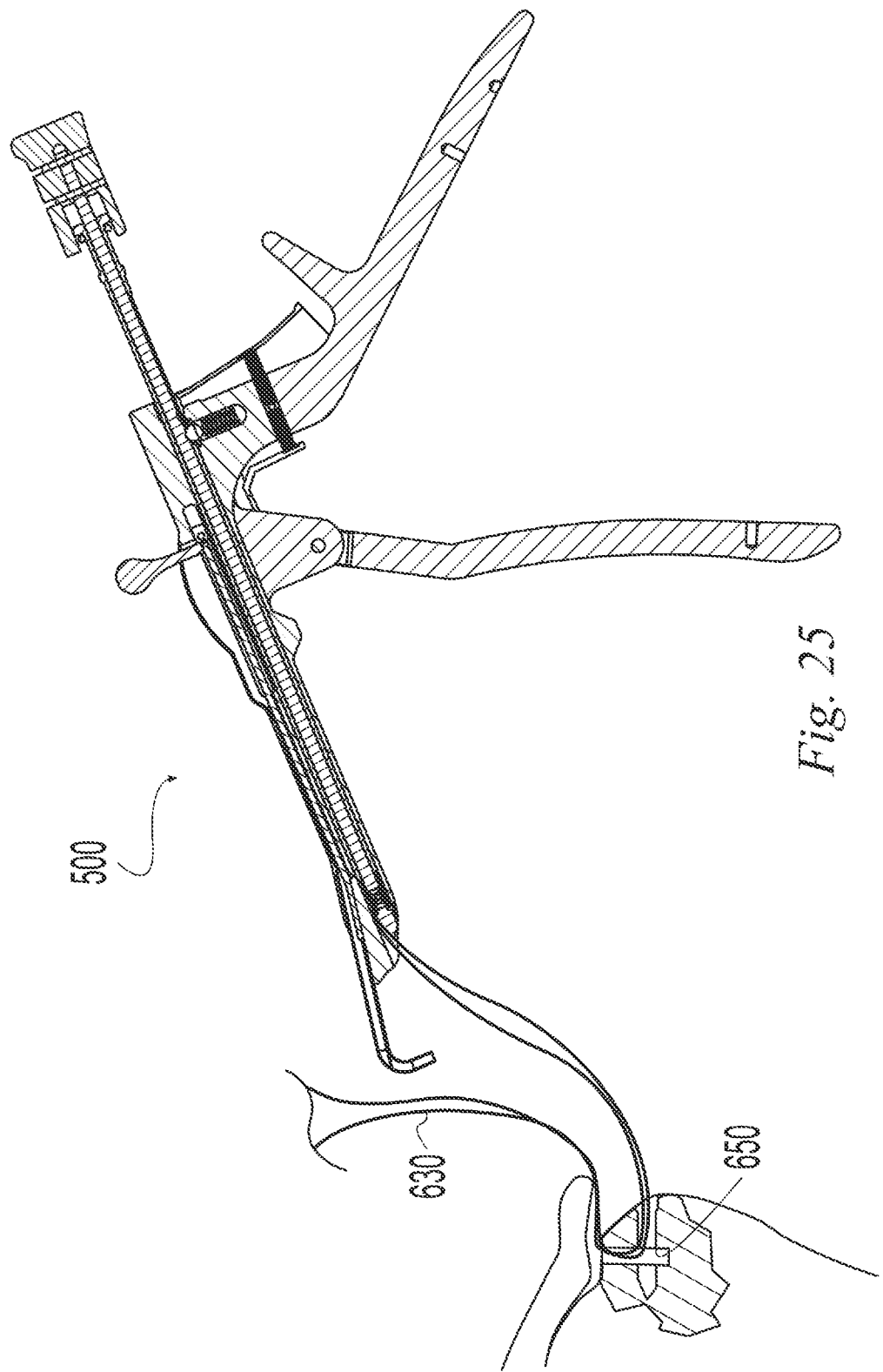

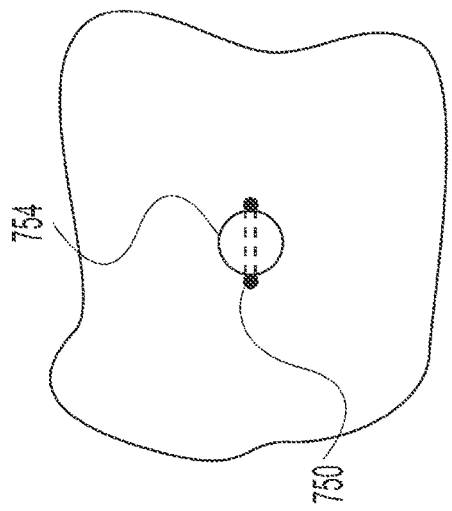
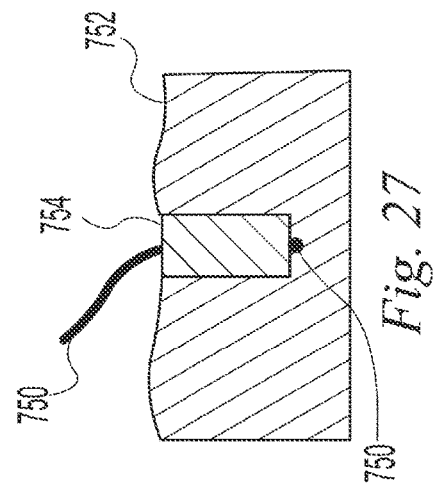
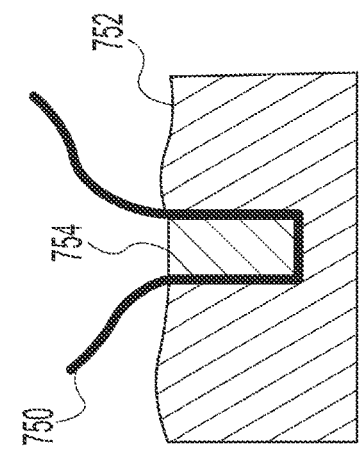

TRANSOSSEOUS ATTACHMENT

CROSS-REFERENCE TO RELATED APPLICATIONS

This application claims the benefit of U.S. Provisional Application No. 61/558,933, filed Nov. 11, 2011 and U.S. Provisional Application No. 61/597,066, filed Feb. 9, 2012, both of which are hereby incorporated by reference.

FIELD OF THE INVENTION

The invention relates to techniques and instruments for surgical transosseous attachments.

BACKGROUND

A variety of surgical procedures require the attachment of something relative to a surgical site. For example, in surgery relating to the skeletal system, it is often advantageous to attach soft tissue, suture, implants, and/or other items in or adjacent to a joint. For example, ligaments, tendons, fascia, other capsular material, and/or muscle may be attached to an adjacent bone to effect a repair of a joint. Such joints may include any joint in a patient's body such as the joints of the hands and feet, ankle, wrist, knee, elbow, hip, shoulder, and spine. For example, it is often advantageous to pass a suture through a portion of a bone to form a transosseous attachment to the bone.

SUMMARY

The present invention provides methods and instruments to attach items to a bone transosseously.

In one aspect of the invention, a method of placing a suture transosseously through a bone includes forming a first bone tunnel in the bone; positioning a portion of a suture in the first bone tunnel; indexing a guide to the first bone tunnel; guiding a tunnel forming instrument with the guide to form a second bone tunnel transverse to and intersecting the first bone tunnel; and withdrawing the portion of the suture through the second bone tunnel.

In another aspect of the invention, instruments for placing a suture transosseously through first and second transverse, intersecting bone tunnels include a guide and a tunnel forming instrument. The guide has a proximal end and a distal end. An indexing portion is formed nearer the distal end and is indexable to a first bone tunnel. The guide defines a guide path from nearer the proximal end to nearer the distal end in predetermined relationship to the indexing portion. The tunnel forming instrument is engageable with the guide in constrained guiding relationship along the guide path. The tunnel forming instrument has a distal end configured to penetrate bone and a suture retrieving portion having a feature able to receive a suture from the first tunnel for retrieval through the second tunnel.

BRIEF DESCRIPTION OF THE DRAWINGS

Various examples of the present invention will be discussed with reference to the appended drawings. These drawings depict only illustrative examples of the invention and are not to be considered limiting of its scope.

FIGS. 4-11 are partial side sectional views of the set of instruments of FIG. 1 in use to pass a suture through a bone;

FIGS. 20-25 are side section views of the instrument of FIG. 17 in use to pass a suture through a bone;

FIG. 26 is a side section view illustrating a method of fixing a suture to a bone using the instruments of FIG. 1;

FIG. 27 is a side section view, rotated 90 degrees from that of FIG. 26;

FIG. 28 is a top plan view of the method of FIG. 26;

DESCRIPTION OF THE ILLUSTRATIVE EXAMPLES

Minimally invasive surgery is surgery used to gain access to deeper parts of the human body through small incisions. Such surgery may range from mini-open surgery to arthroscopic surgery. Mini-open surgery is generally understood to mean surgery performed through small incision(s) under direct vision as opposed to arthroscopic (or endoscopic) surgery where surgery is performed through one or more stab incisions in which the arthroscope (or endoscope) is used for visualization. In arthroscopic surgeries, the size of the stab incisions generally ranges from 1 mm to 10 mm. The illustrative examples depict arthroscopic surgical techniques but it is to be understood that the techniques could be performed in any minimally invasive or open technique. The following illustrative examples depict instruments and techniques to pass a suture through a portion of the head of the humeral bone at the shoulder of a human patient to repair damaged soft tissue associated with the shoulder joint. Instruments and techniques according to the present invention may be used to pass a suture through any bone, at surgical sites anywhere in a patient's body, and for any purpose. The terms "suture" and "suture strand" are used herein to mean any strand or flexible member, natural or synthetic, able to be passed through a bone tunnel and useful in a surgical procedure. The term "transverse" is used herein to mean to cross at an angle; i.e. not parallel. The term includes, but is not limited to right angles. The term "bight" is used herein to mean a bend or loop formed in the intermediate portion of a suture.

A human left shoulder joint is used to provide context for illustrative examples of a surgical technique. The subacromial space, between the humeral head and the undersurface of the acromion, is a potential space for surgical repair. This space is partially occupied by the subacromial bursa. Soft tissue layers overlie the shoulder joint. These layers define a soft tissue zone including the skin, subcutaneous tissue, muscles and bursal tissue. Instruments are inserted through the soft tissue zone via stab incisions and access canulae can be inserted through these stab incisions to facilitate the insertion and withdrawal of surgical instruments. The thickness of this soft tissue zone varies by patient and by location from a few millimeters to several centimeters.

Figure 1:
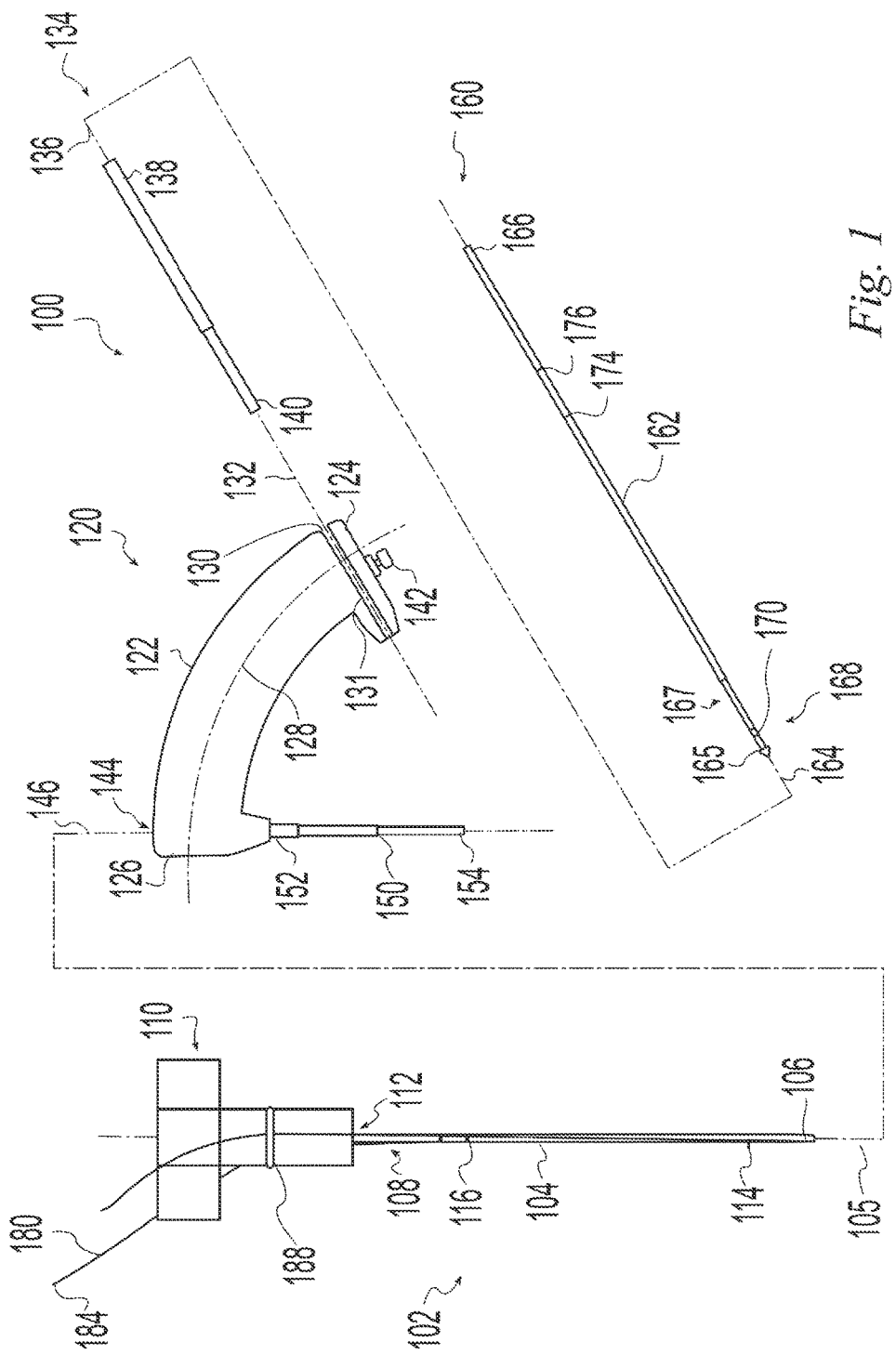
FIG. 1 is a side elevation view of a set of instruments according to the present invention.
Figure 2:
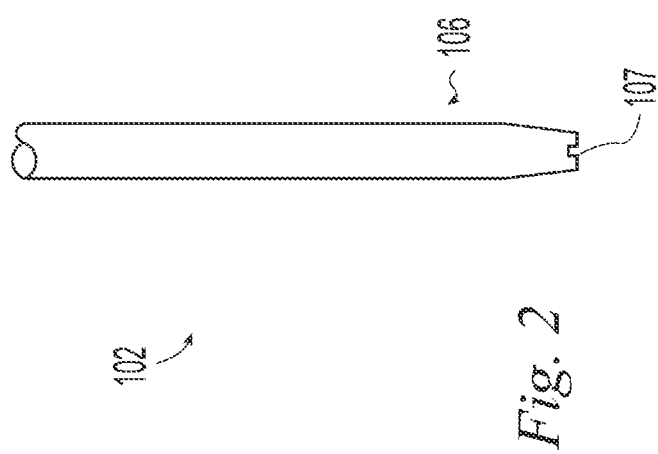
FIG. 2 is a detail view of a portion of one of the instruments of FIG. 1.

Referring to FIG. 1, a set of instruments 100 includes a punch 102, a tunnel guide 120, and a retriever 160. The punch 102 includes an elongated shaft 104 extending from a first, distal end 106 to a second, proximal end 108 along an axis 105. A punch handle 110 includes an opening 112 for receiving the proximal end 108. The punch handle 110 is able to lock onto the punch 102, e.g. with a rotating collet arrangement, to facilitate inserting the distal end 106 of the punch into tissue and removing it from tissue. The distal end 106 includes a notch 107 to aid in retaining a suture on the end as the suture is impacted into a bone as shown in FIG. 2.

The tunnel guide 120 includes an arm 122 extending from a first end 124 to a second end 126 along an axis 128. In the illustrative example of FIG. 1, the axis is arcuate. The first end 124 defines a passage 130 having an axis 132 transverse to the arm axis 128 and open along a slot 131 on one side. A retriever sleeve 134 has a longitudinal axis 136 extending between a first, proximal end 138 and a second, distal end 140. The retriever sleeve 134 is received in the passage 130 in axial translating relationship and is infinitely adjustable along its axis relative to the passage 130. Preferably the sleeve 134 fits closely within the passage 130 and is larger than the slot 131 so that the sleeve cannot pass sideways out of the passage 130. A lock 142 is operable to lock the retriever sleeve 134 position relative to the passage 130. In the illustrative example, the lock 142 is a screw threaded into the first end 124 adjacent and transverse to the passage axis 132 and in communication with the passage 130 such that it is responsive to inward threading to advance toward and press against the retriever sleeve 134 and lock it in place. The second end 126 defines a passage 144 through the arm 122 having a longitudinal axis 146 transverse to the arm axis 128 and generally coplanar with the passage axis 132. The axes 146 and 132 converge on the concave side of the arcuate arm axis 128.

The exemplary guide 120 has a non-adjustable arm 122 maintaining the axes 132 and 146 in fixed angular relationship. The arm 122 may also include an adjustment mechanism allowing the angle between the axes 132 and 146 to be adjusted by the user to accommodate variations in patient anatomy and placement technique.

An indexing feature is provided to register the guide 120 to a first bone tunnel in preparation for forming a second bone tunnel in known relationship to the first bone tunnel. In the illustrative example of FIGS. 1-11, the indexing feature is in the form of a punch Sleeve 150. The punch sleeve 150 has a proximal end 152, a distal end 154, and an axial passage extending between the proximal and distal ends. The punch sleeve 150 is mounted coaxially in the passage 144 and extends distally from the arm 122 such that the punch sleeve 150 and passage 130, and consequently the sleeve 134 when it is received in the passage 130, converge distally.

The retriever 160, includes an elongated shaft 162 extending along an axis 164 from a first, proximal end 166 to a second, distal end 168. The distal end 168 has a distal, leading segment 165 and a proximal, narrowed segment 167 in which the diameter of the narrowed segment 167 is generally less than the maximum diameter of the leading segment 165. When the retriever 160 is inserted into bone, a bony tunnel is created in accordance to the maximum cross-sectional profile of the leading segment 165. The resistance to withdrawal of the impacted retriever 160 is reduced as there is reduced or no friction between the wall of the bone tunnel and the narrowed segment 167. A notch 170 is formed in the side of the shaft 162 near the distal end 168. The retriever is sized to fit within the retriever sleeve 134 and to pass sideways out of the passage 130 through the slot 131 when the retriever sleeve is not positioned in the passage 130.

Figure 3:
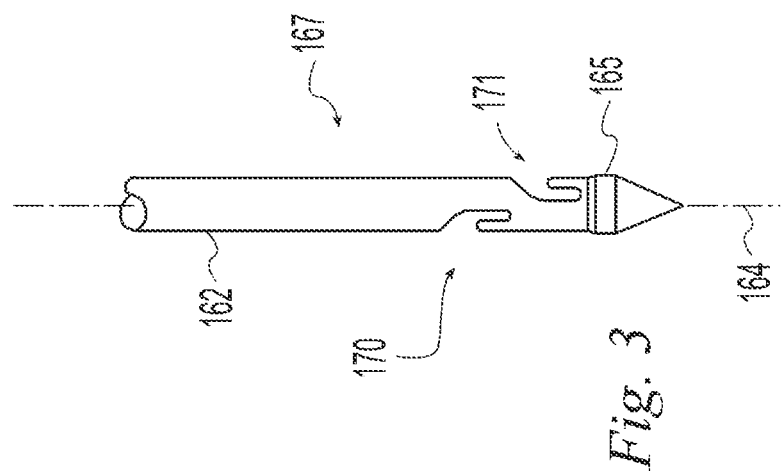
FIG. 3 is a detail view of a portion of one of the instruments of FIG. 1.

FIG. 3 illustrates one example of the notch 170. In this illustrative example, the notch 170 is formed into the side of the shaft transverse to the axis 164 and then extends distally parallel to the axis 164. Additional notches, such as illustrative second notch 171, may be formed on the shaft to aid in suture retrieval. In the illustrative example of FIG. 3, a second notch 171 is formed 180 degrees and distally from the first notch 170. The one or more notches may be located within the narrowed segment 167 to reduce the likelihood of the proximal edges of the notches 170, 171 snagging against the wall of the bone tunnel.

FIGS. 4-10 illustrate an exemplary technique using the instruments of FIG. 1. The punch is setup as shown in FIG. 1. The punch handle 110 is attached to the punch shaft 104. A suture 180 is mounted to the punch 102 by passing a portion 182 of the suture over the distal end 106 of the punch in the notch 107 and positioning the ends 184 of the suture toward the proximal end 108 of the punch. The ends 184 may be retained and/or placed in tension by engaging them with a retention mechanism such as a slot, boss, O-ring, and/or other mechanism into which or around which they may be positioned to maintain the suture 180 on the punch 102. For example, in the example of FIGS. 1-11, an O-ring 188 is mounted on the handle 110 and the suture 180 is run under the O-ring 188 to retain the suture 180.

The punch 102 is inserted into bone tissue. This may be accomplished by optionally predrilling the bone and then inserting the punch, or, as illustrated in the exemplary technique of FIGS. 2-8, the punch 102 may be inserted directly into the bone such as for example by impacting the handle 110 with a mallet to drive the distal end 106 into the bone.

In the exemplary technique of FIGS. 4-11, a shoulder 200 repair surgical procedure is illustrated such as for, for example, attaching soft tissues of the rotator cuff 201 to the proximal humerus 202. The punch 102 and suture 180 are introduced into the surgical site and the distal end 106 of the punch 102 is placed against the proximal humerus 202 at a desire suture exit location. The punch 102 and suture 180 may be inserted percutaneously through a small stab incision.

Figure 4:
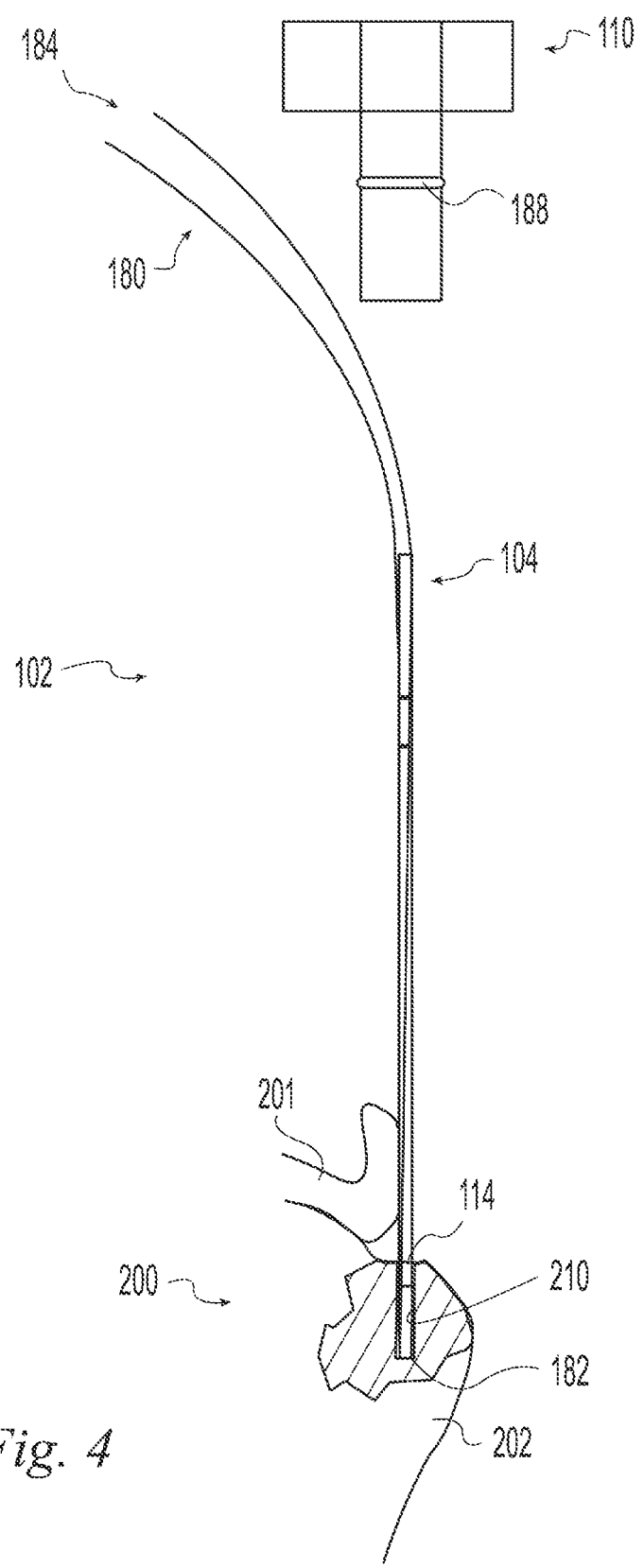

As shown in FIG. 4, the punch 102 and suture 180 are impacted into the bone tissue by impacting the punch handle 110 to drive the distal end 106 to a predetermined depth into the bone and to form a first bone tunnel 210. In the illustrative technique, the punch and suture are driven approximately 18 mm into the bone. An index mark 114 may be provided a predetermined distance from the distal end 106 as a reference. The handle 110 is unlocked and removed from the punch shaft 104.

Figure 5:
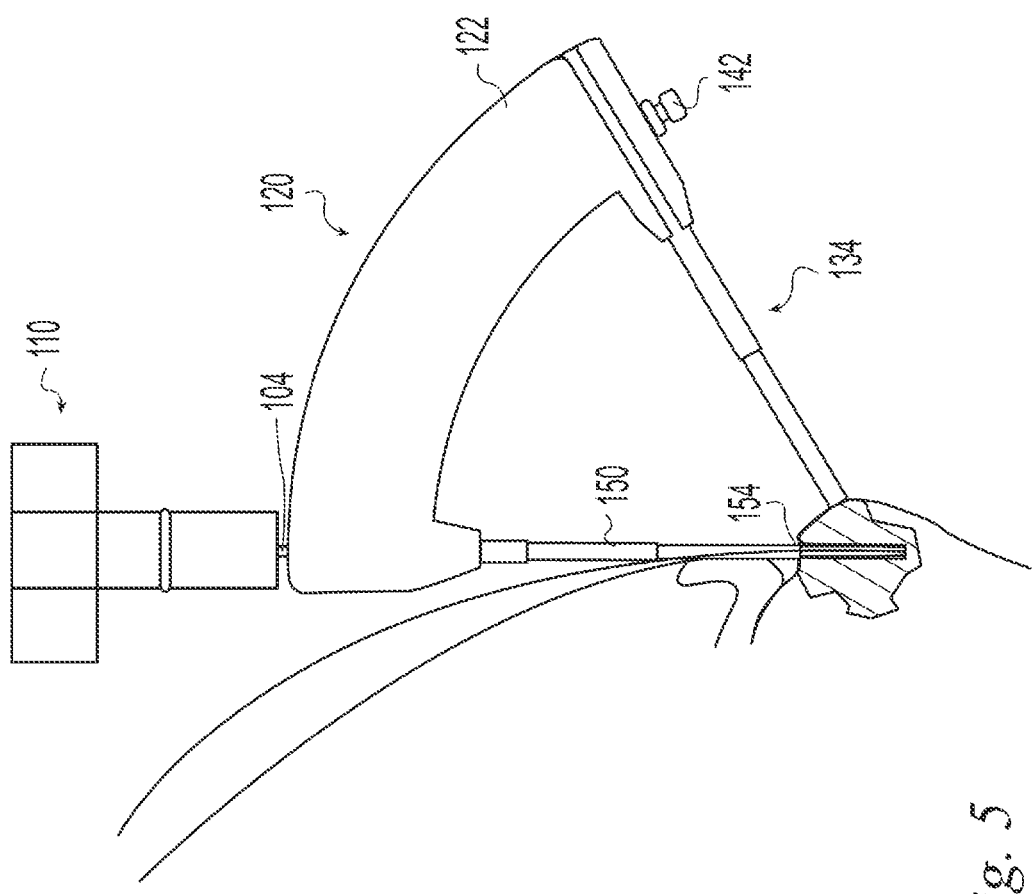

Referring to FIG. 5, the tunnel guide 120 is engaged with the punch shaft 104 by sliding the distal end 154 of the punch sleeve 150 over the proximal end 108 of the shaft 104 and advancing the tunnel guide 120 toward the bone until distal end 154 of the punch sleeve 150 is brought to rest against the bone. The handle 110 is remounted to the punch shaft 104. The retriever sleeve 134 is engaged with the passage 130 in the arm 122 and advanced percutaneously into the surgical site until it rests against the bone. The lock 142 is actuated to lock the sleeve 134 in place.

Referring to FIG. 6, the retriever 160 is advanced toward the punch 102. This may be accomplished by optionally predrilling the bone through the retriever sleeve and then inserting the retriever 160, or the retriever 160 may be inserted directly into the bone. In the illustrative example of FIG. 6, the retriever 160 is introduced to the surgical site through the retriever sleeve 134 until the distal end 168 is adjacent the bone. It is then impacted into the bone forming a second bone tunnel 212. It is impacted to a first predetermined depth in which the distal end 168 is spaced from the punch shaft 104. An index mark 174 on the retriever shaft 162 may be provided a predetermined distance from the distal end 168 as a reference. For example, the index mark 174 may be referenced to the arm 122 to indicate that the predetermined depth has been reached.

Referring to FIGS. 7 and 8, the punch 102 is withdrawn a predetermined distance to provide clearance for the retriever. An index mark 116 may be provided a predetermined distance from the distal end 106 as a reference. For example, the index mark 116 on the punch shaft 104 may be referenced to the arm 122 to indicate that withdrawal the predetermined distance has been accomplished. FIG. 8 is a cross sectional view looking along the axis of the retriever toward the punch 102. The suture 180 is pressed into the bone and adheres to the bone when the punch 102 is driven such that when the punch 102 is withdrawn, the suture 180 remains in the depth of the punched hole forming a loop 186.

Referring to FIG. 9, the retriever 160 is then advanced further into the bone to a second predetermined depth in which the distal end 168 intersects the loop 186 of suture. An index mark 176 may be provided to indicate the second predetermined depth. The lock 142 is now disengaged to release the sleeve 134 and the sleeve 134 is withdrawn proximally from the passage 130 and removed. The arm 122 may now be rotated away from the retriever so that the retriever exits the passage 130 via the slot 131 thus freeing the arm 122, punch sleeve 150, and punch 102 to be withdrawn axially away from the bone and removed from the surgical site.

Figure 11:
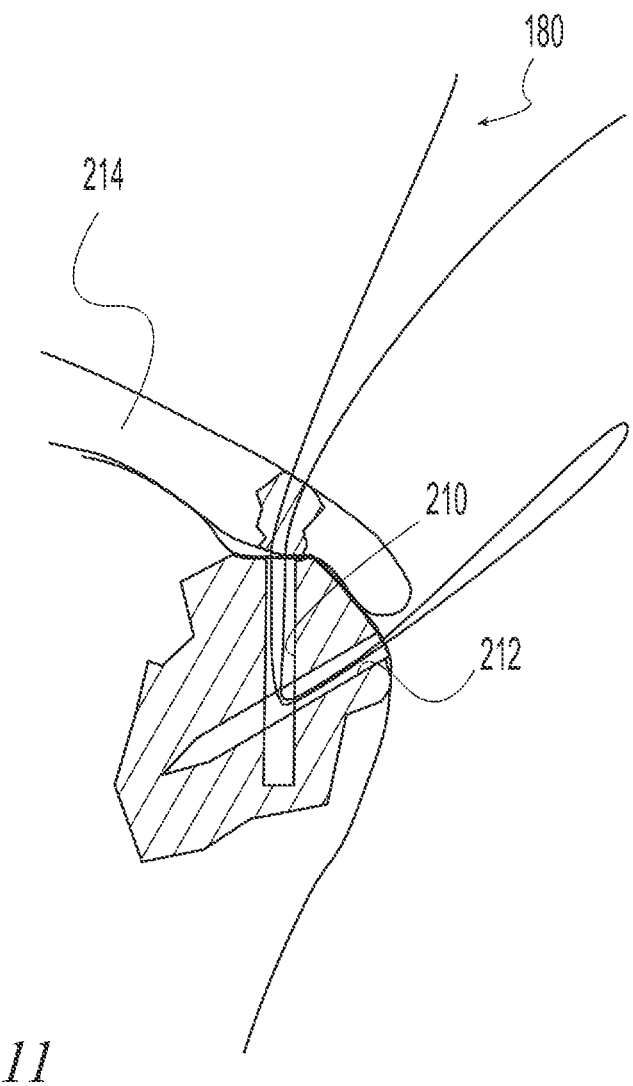

Referring to FIGS. 10 and 11, the suture 180 is tensioned to pull the loop 186 against the side of the retriever. The retriever is withdrawn so that the notch 170 engages the suture loop 186 and pulls the suture loop 186 through the second bone tunnel 212 such that the suture passes through the bone and extends outwardly from both the first and second bone tunnels 210, 212. The suture 180 may now be passed through soft tissue 214 adjacent the bone and used to connect the soft tissue to the bone such as by tying the suture, passing it over a button, and/or some other suture fastening technique.

Figure 12:
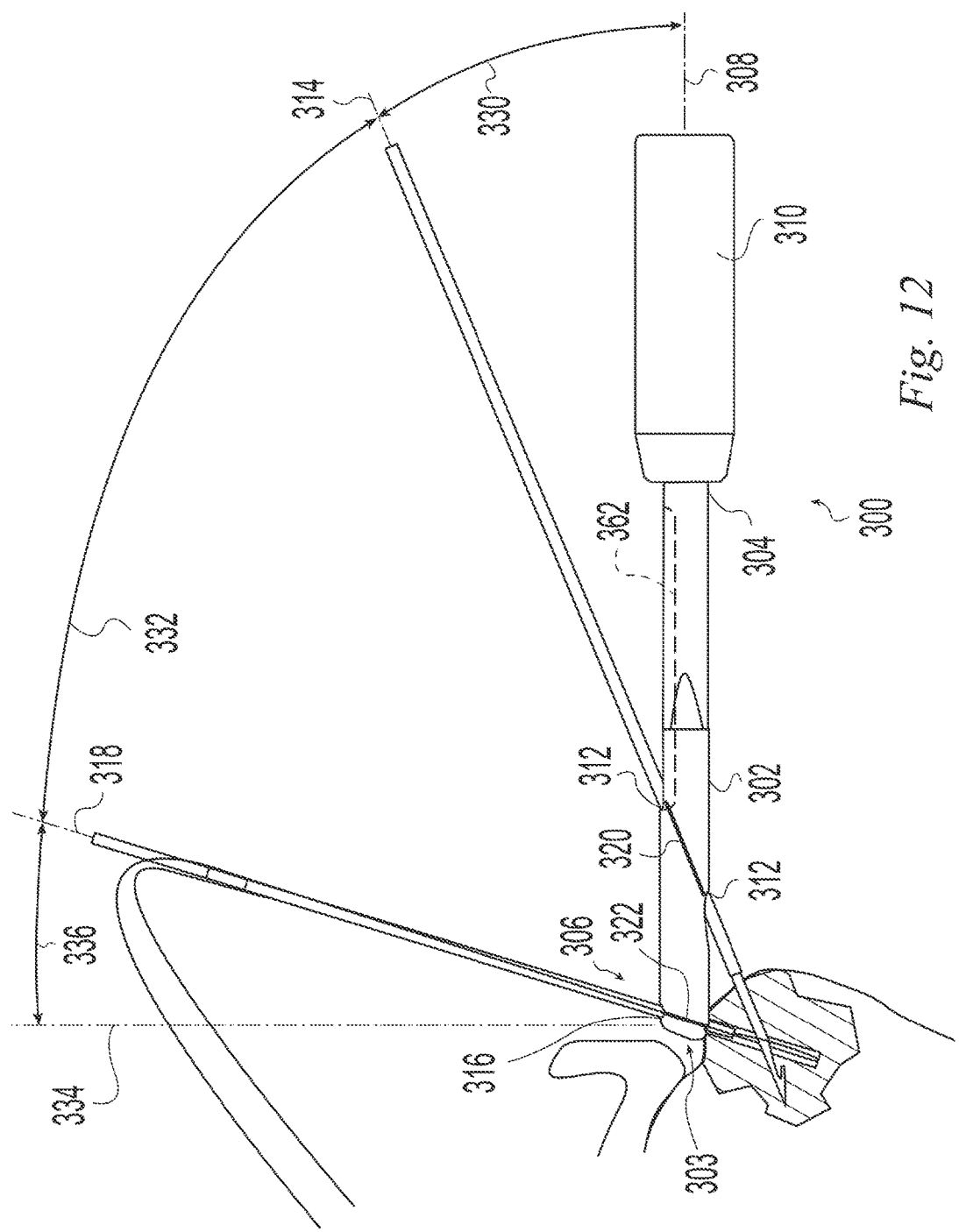
FIGS. 12 and 13 are partial side sectional views of a set of instruments similar to that of FIG. 1 illustrating an alternative arrangement for one of the instruments.
Figure 13:
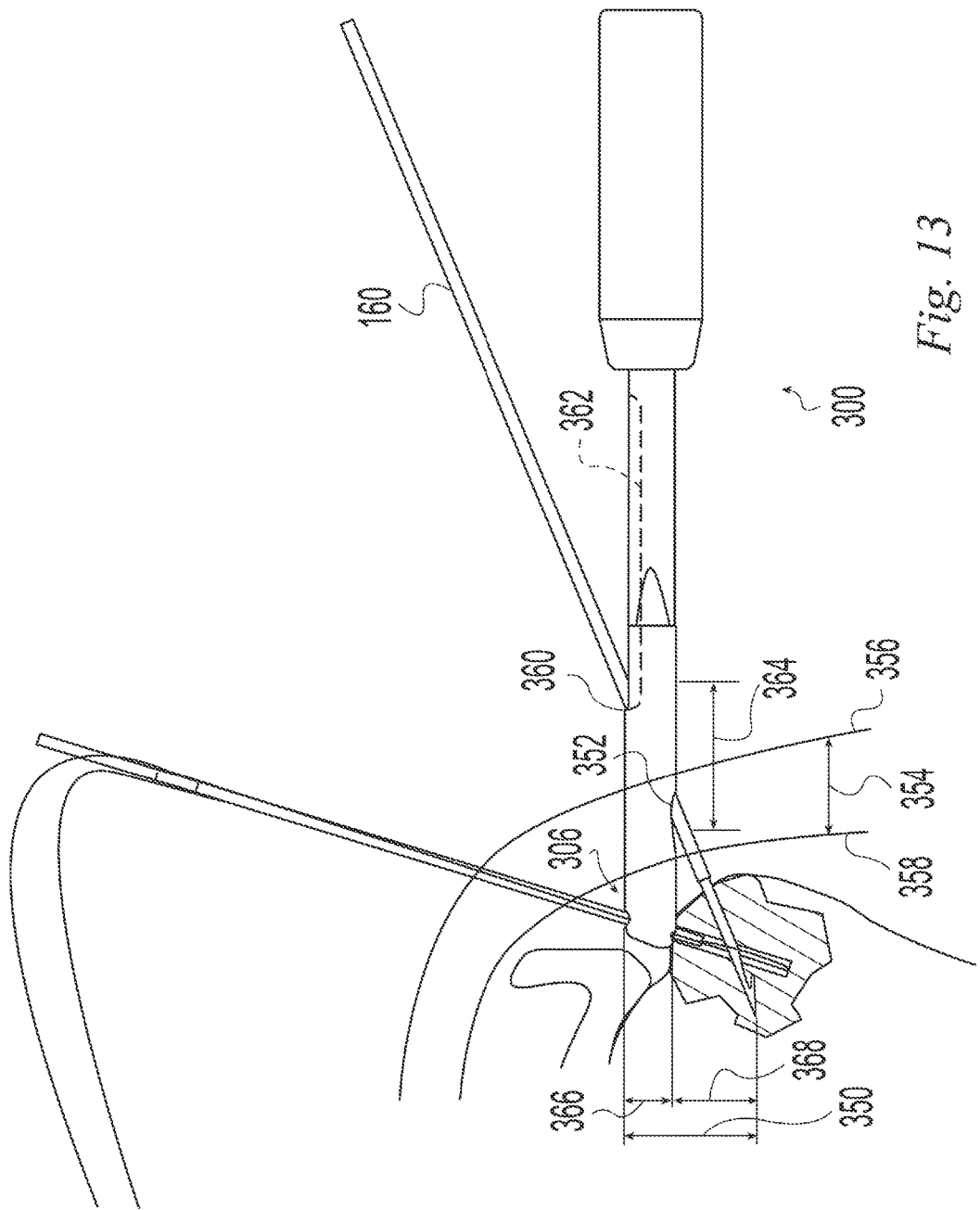

FIGS. 12 and 13 depict an illustrative set of instruments similar to the example of FIG. 1 that is modified to have a reduced size. A tunnel guide 300 includes a shaft 302 extending from a first, proximal end 304 to a second, distal end 306 along an axis 308. The distal end 306 defines a head member 307. A handle 310 is mounted to the proximal end 304. A retriever guide passage 312 is formed transversely through the shaft 302 along an axis 314. An indexing feature in the form of a punch guide passage 316 is formed transversely through the head member 307 along an axis 318 distal to the retriever guide passage 312. Index marks 320 and 322 are provided on the exterior of the shaft aligned with and parallel to the passage axes 314, 318 to aid in visualizing the passage paths.

The retriever guide passage 312 forms an angle 330 with the shaft axis 308. The retriever guide passage angle 330 is between 0 and 90 degrees, preferably between 10 and 30 degrees. In the illustrative example of FIGS. 12 and 13, the retriever guide passage angle 330 is approximately 20 degrees. Likewise, the punch guide passage 316 forms an angle 332 with the retriever guide passage 312. The angle between the passage axes 318, 314 is preferably between 0 and 90 degrees, more preferably between 30 and 70 degrees. In the illustrative example of FIGS. 12 and 13, the punch guide passage 316 is angled approximately 50 degrees relative to the retriever guide passage 312. Referenced in a different way, in the illustrative example of FIGS. 12 and 13, the punch guide passage is angled proximally at an angle 336 of approximately 20 degrees from a reference line 334 normal to the shaft axis 308.

Optionally, a groove 362 is formed in the shaft 302 and extends lengthwise along a portion of the shaft 302 until it intersects the external exit opening 360. The groove 362 facilitates locating the retriever guide passage even if the retriever guide passage is covered by soft tissue such as the margins of the percutaneous portal to the surgical site. For example, the retriever 160 may be positioned by sliding the distal end of the retriever distally along the groove, and under the soft tissue as necessary, until the retriever guide passage is engaged at the external exit opening 360. The retriever 160 may then be advanced towards the humeral head. The groove 362 allows the retriever 160 to be placed tactilely without direct visualization where anatomy or technique requires.

Referring to FIG. 13, optionally, but advantageously sharp portions of the lead profile are minimized to reduce the risk of snagging soft tissue during insertion. A soft tissue zone 354 is defined as the space between the skin 356 and soft tissues 358 near the bone; e.g. the humeral head. The axial spacing of the internal and external exit openings 352, 360 of the retriever guide passage 312 defines a protected guide path 364 over which the surrounding soft tissue is protected from the retriever 160. Optionally, but advantageously, the internal exit opening 352 on the tunnel guide is placed in close proximity to the surgical site to maximize the protected guide path 364 and avoid interference with the soft tissue zone 354 near the surgical site. Optionally, but advantageously, the external exit opening 360 on the tunnel guide is placed as proximal (nearer the proximal handle portion) as possible to maximize the protected guide path 364 and better accommodate large or obese patients having a wide soft tissue zone 354.

One way to move the internal exit opening 352 close to the surgical site is by reducing the lead profile height 350 which is defined as the vertical distance from the superior surface of the distal end 306 of the tunnel guide 300 to the inferior aspect of the distal end of the retriever 160 when it is inserted to its full operating depth in the bone. An indexing height 366 is defined as the vertical distance from the superior surface of the distal end 306 of the tunnel guide 300 to the inferior surface of the distal end 306 of the tunnel guide 300. A vertical bone depth 368 is defined as the vertical distance from the inferior surface of the distal end 306 of the tunnel guide 300 to the inferior aspect of the distal end of the retriever 160 when it is inserted to its full operating depth in the bone. In the illustrative example of FIG. 13, the indexing height 366 and vertical bone depth 368 stack up to make up the lead profile height 350. Although the distance from the internal exit opening to the surgical site is preferably minimized, there is a limit because a minimum angle between the first and the second bone tunnels needs to be maintained to ensure a sufficiently long suture bridge in the bone to provide adequate suture pull out strength. There is also a desired minimum vertical bone depth to create a first bone tunnel of a predetermined depth. However, the indexing height 366 can be reduced to decrease the lead profile height.

Figure 14:
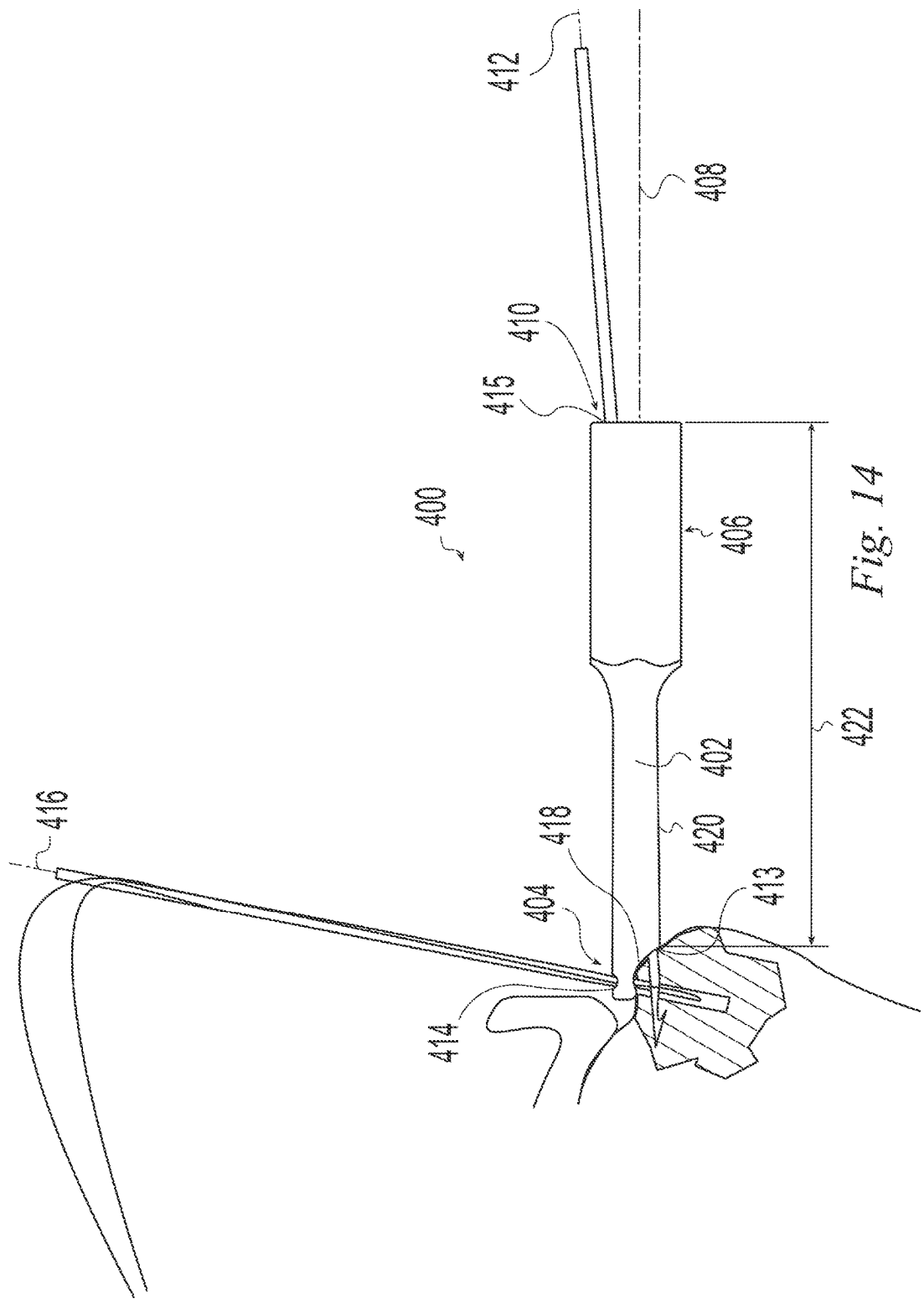
FIG. 14 is a partial side sectional view of a set of instruments similar to that of FIG. 1 illustrating an alternative arrangement for one of the instruments.

FIG. 14 illustrates another example of a tunnel guide 400 similar to that of FIGS. 12 and 13 but with a further reduced indexing height. The tunnel guide 400 includes a shaft 402 extending from a distal head member 404 to a proximal handle member 406 along an axis 408. A retriever guide passage 410 is formed transversely through the shaft member and the handle member along a retriever guide passage axis 412 and defines internal and external exit openings 413, 415. The retriever guide passage axis 412 forms an angle with the shaft axis 408.

An indexing feature 414 is formed transversely through the head member 404 along an indexing feature axis 416. The indexing feature axis 416 also forms an angle with the retriever guide passage axis 412. In the illustrative example of FIG. 14, the indexing feature is a punch guide passage. The passage may be a simple cylinder or have one or more additional slots formed on the sidewall of the passage to provide clearance for sutures alongside the punch. The indexing feature may take other suitable forms such as an open notch or a probe tip. In the illustrative example of FIG. 14, the inferior surface 418 of the head member 404 is superior to the inferior surface 420 of the shaft member whereas in the illustrative example of FIG. 13, the inferior surface of the head member is level with the inferior surface of the shaft member. Preferably, the inferior surface 418 of the head member as illustrated in FIG. 14 has a curvature which approximately fits the contour of the bone at the surgical site. For example, for use in rotator cuff repair surgery, the curvature would fit the greater tuberosity of the humeral head such that the internal exit opening 413 of the tunnel guide is in close proximity to the surgical site. When the head member of the tunnel guide is thinner than the shaft member, as shown in FIG. 14, the internal exit opening 413 can be kept close to the surgical site while decreasing the angle between the tunnel guide axis 408 and the retriever axis 412. As a result, the external exit opening 415 may be located on the proximal end of the handle member 406 of the tunnel guide and the protected guide path 422 is lengthened as compared to the example of FIG. 10 and can accommodate an even wider soft tissue zone.

Figure 15:
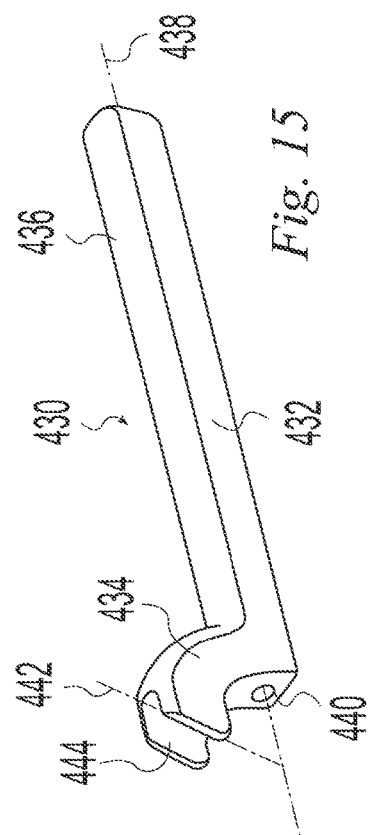
FIG. 15 is a perspective view illustrating an alternative arrangement for one of the instruments of FIG. 1.

FIG. 15 illustrates another example of a tunnel guide 430 which lengthens the protected guide path to the maximum, without over-thinning of the head member. In the illustrative example in FIG. 12, the tunnel guide 430 includes a shaft member 432 extending from a distal head member 434 to a proximal handle member 436 along a tunnel guide axis 438. The distal head member 434 of the tunnel guide is curved. The undersurface of the distal head member is contoured to approximately fit the greater tuberosity of the humeral head.

A retriever guide passage 440 is formed through the shaft member 432 and the handle member 436 coaxial with the tunnel guide axis 438. When the head member of the guide is positioned on the greater tuberosity, the tunnel guide axis 438 is approximately level with the surgical site.

An indexing feature is formed transversely to the head member along an indexing feature axis 442. The indexing feature axis 442 forms an angle with the tunnel guide axis 438. In the illustrative example of FIG. 15, the indexing feature is a U-shaped slot 444 engageable with a tunnel forming instrument such as the punch of FIG. 1. Because the U-shaped slot 444 is open on one side, the first bone tunnel can be formed before the guide 430 is introduced to the surgical site. The guide can then be engaged with the tunnel forming instrument by introducing it, e.g., through a second soft tissue portal and sliding it sideways into engagement with the tunnel forming instrument. The procedure may then be carried out as described relative to the other examples. Alternatively the indexing feature can also be a punch guide passage that is engaged axially over the end of the first tunnel forming instrument to index the guide as in the previous examples or the indexing feature may be a probe engageable with a first bone tunnel upon removal of the first bone tunnel forming instrument to index the guide to position it for forming the second bone tunnel and retrieving a suture.

Figure 16:
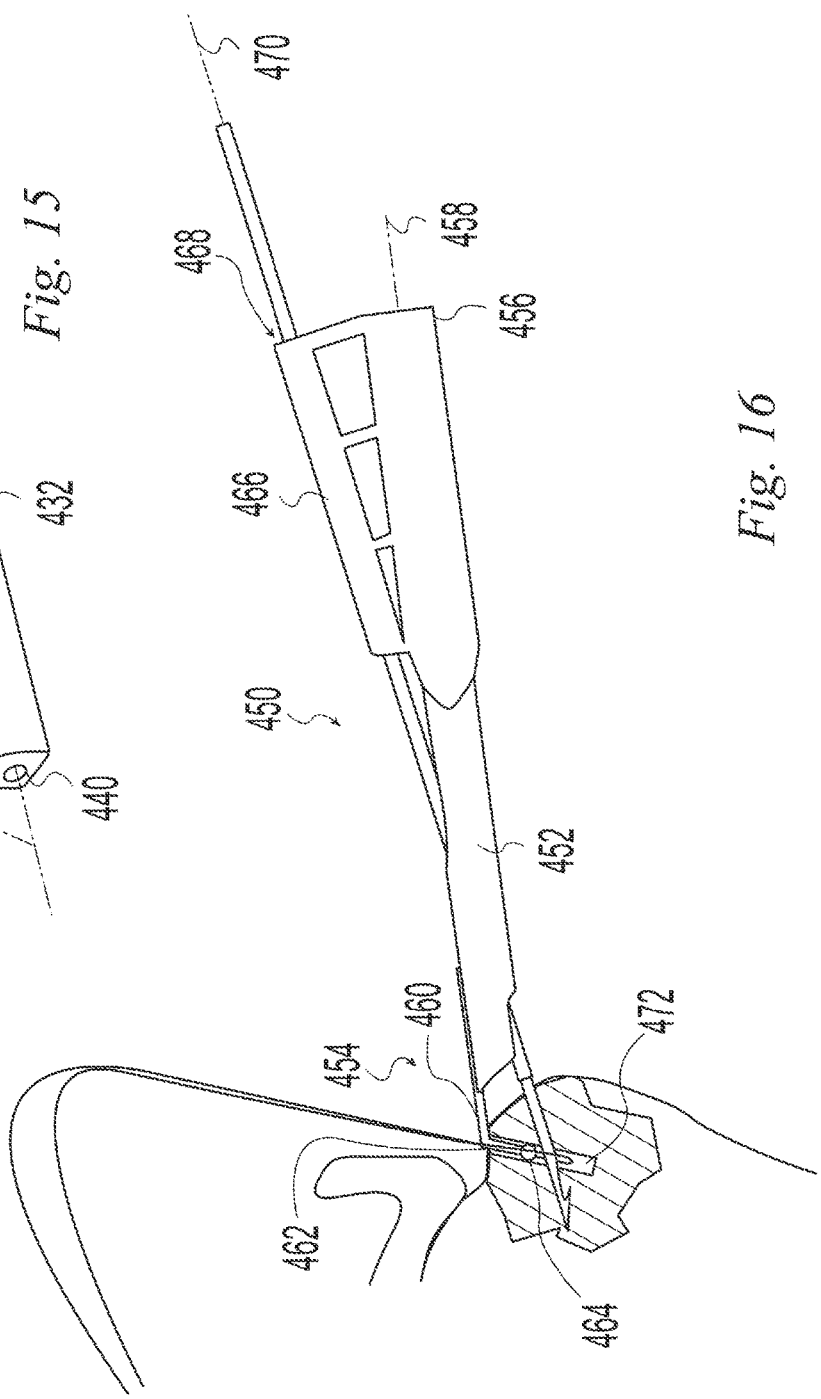
FIG. 16 is a partial side sectional view illustrating an alternative arrangement for one of the instruments of FIG. 1.
Figure 17:
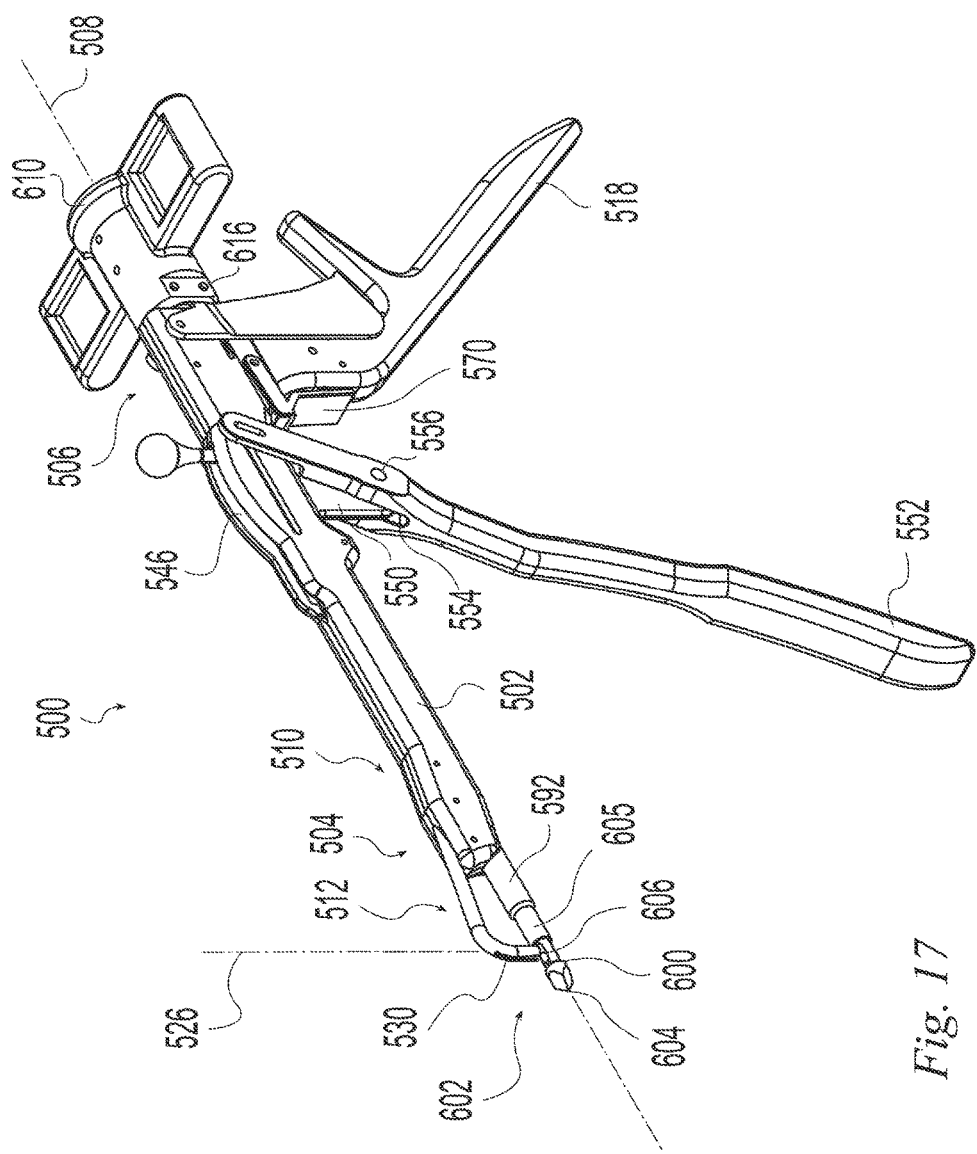
FIG. 17 is a perspective view of an instrument according to the present invention.

FIG. 16 illustrates another illustrative example of a tunnel guide. The tunnel guide 450 includes a shaft member 452 extending between a distal head member 454 and a proximal end 456 along a shaft axis 458. The distal head member 454 has an indexing feature in the form of a blunt-ended probe engageable with a first bone tunnel. The blunt-ended probe comprises a shaft 462 and a bulbous tip 464 at the distal end of the shaft 462. The bulbous tip 464 is sized to engage the first bone tunnel in close fit sliding relationship. The resistance to insertion of the probe 460 is reduced as there is reduced or no friction between the wall of the bone tunnel and the shaft which is smaller than the tip. The length of the probe is significantly less than the depth of the first bone tunnel so that the bulbous tip will not intersect the projected retriever guide axis. On the upper side of the shaft member there is a generally triangular fin 466.

A retriever guide passage 468 is formed transversely through the shaft member and the fin along a retriever guide axis 470. The retriever guide axis 470 forms an angle with the shaft axis 458. When the head member of the guide is positioned near the greater tuberosity, the shaft axis is approximately level with the surgical site.

In use, a first bone tunnel 472 is formed and a suture loop is delivered into the first bone tunnel 472. For example, the suture loop may be delivered simultaneously with punching the tunnel or it may be delivered after the tunnel is formed. The probe 460 is inserted into the first bone tunnel and the retriever is advanced to the surgical site along the retriever guide passage to intersect the first bone tunnel and suture loop and retrieve the suture through a second bone tunnel.

FIGS. 17-25 illustrate another illustrative example of a tunnel guide. The tunnel guide 500 includes a shaft member 502 extending between a distal end 504 and a proximal end 506 along a shaft axis 508. The distal end defines a distal head member 510 having an indexing feature in the form of a tubular probe 512 engageable with a first bone tunnel. The shaft member 502 includes a retriever guide passage 514 (FIG. 20) coaxial with the shaft axis 508 and extending between the proximal and distal ends 506, 504. The shaft member 502 includes a suture passer guide passage 516 parallel to the shaft axis 508 and extending from the distal end 504 toward the proximal end 506. A retriever assembly 590 (FIG. 20) is mounted to the shaft member 502 for translation within the retriever guide passage 514. A suture passer assembly 534 (FIG. 20) is mounted to the shaft member 502 for translation within a suture passer guide passage 516. A handle 518 extends transversely, downwardly from the shaft member and provides a grip for the tunnel guide. Each feature and assembly of the tunnel guide 500 will be described more fully below.

Figure 20:
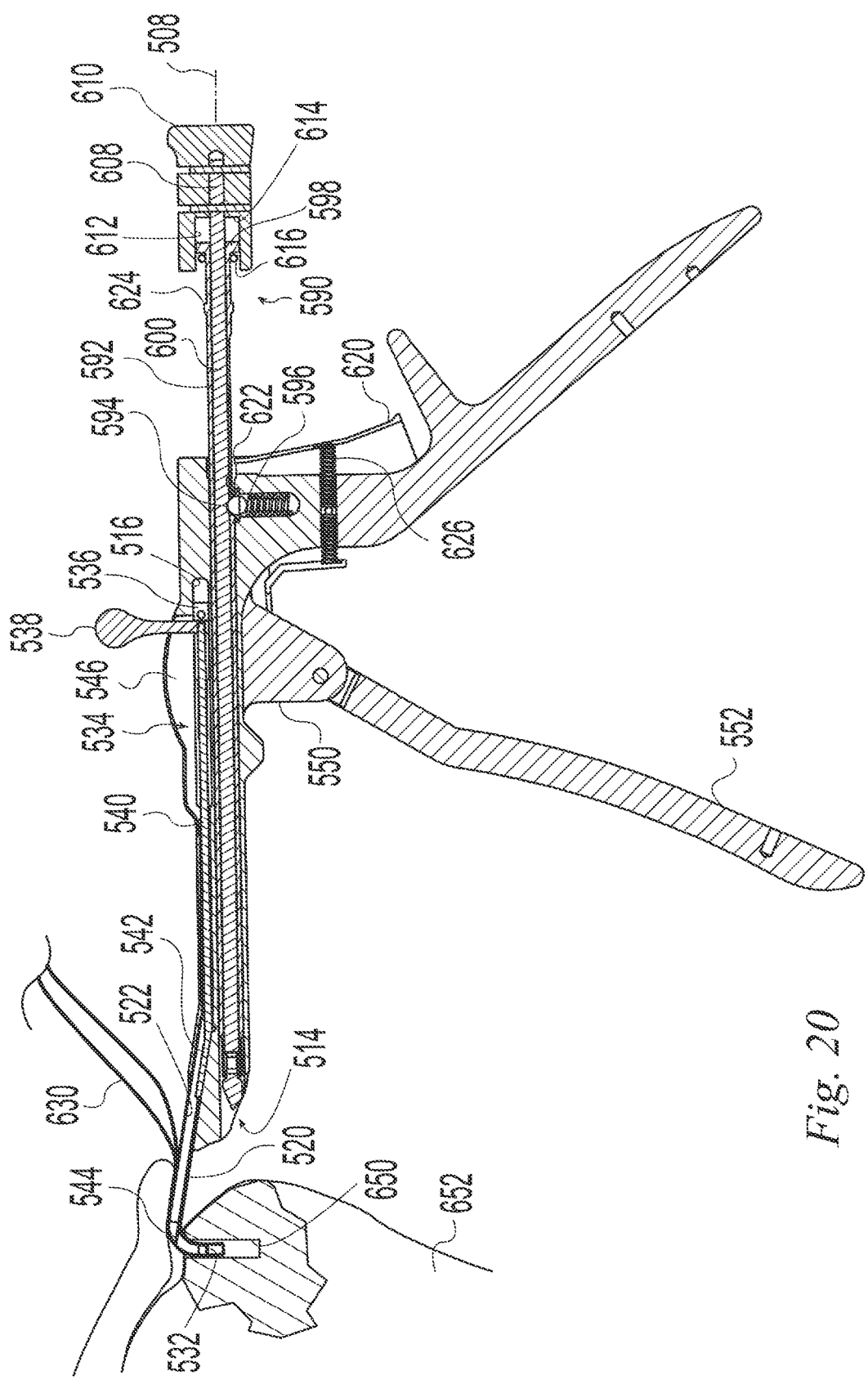

The tubular probe 512 indexing feature includes a bent tube 520 mounted to and extending distally from the head member 510. The tube 520 has an internal lumen 522 communicating with the suture passer guide passage 516 (FIG. 20). The tube 520 diverges distally away from the shaft axis 508 and then bends back toward the shaft axis to form a hooked distal end 524 (FIG. 18) having a probe tip axis 526. The probe tip axis 526 (FIG. 18) forms an angle with the shaft axis 508. In the illustrative example of FIGS. 14-22, the probe tip axis 526 is at an angle of approximately 90 degrees to the shaft axis 508 and has a probe tip exit opening 528. A suture slot 530 (FIG. 17) is formed in the distal end 524 of the probe to receive a suture portion 532 (FIG. 20) to position the suture portion 532 transverse to the internal lumen 522.

The suture passer assembly 534 is mounted for axial translation within the suture passer guide passage 516 and tube 520. The suture passer assembly 534 is releasably received by a carriage 536 and includes a suture passer having a handle 538 and a shaft 540 mounted to the handle 538. The suture passer shaft 540 has a flexible portion 542 ending in a tip 544. In the illustrative example of FIGS. 17-25, the flexible portion 542 and tip 544 are ribbon shaped to facilitate bending in one direction to follow the curvature of the bent tube 520. In the illustrative example of FIGS. 17-25, the suture passer assembly 534 is inserted into the suture passer guide passage 516 through a slot 546 (FIG. 17) and engaged with the carriage 536 such that the suture passers may be provided as easily replaceable modular units.

A tab 550 extends below the shaft member 502. A trigger 552 is mounted to the tab 550 for rotation. The trigger 552 includes a yoke 554 (FIG. 17) that straddles the tab and a pin 556 through the yoke and tab defines the rotation axis of the trigger. The ends 558, 560 of the yoke 554 (FIGS. 18 and 19) include longitudinal slots 562, 564, oriented radially from the center of the pin 556. A pin 566 through the carriage 536 is received in the slots 562, 564. As the trigger is rotated, the pin 566 follows the slots 562, 564 and converts the trigger rotation into linear translation of the carriage 536. As the carriage translates distally, it drives the suture passer assembly 534 distally causing the suture passer shaft 540 to bend as it follows the curve of the tube 520. Further motion of the suture passer assembly 534 causes the tip 544 to engage the suture portion 532 and pass it distally off of the tube 520 and away from the tube generally along the probe tip axis 526. Means for engaging the suture portion 532 by the tip 544 include one or more notches on the side of the tip or a notch located at the very distal portion of the tip. Such notches may be oriented in a manner such that the suture portion 532 is snared by the notch as the tip 544 moves distally and the suture portion 532 is released when the tip 544 is retracted. A trigger lock 570 (FIG. 19) may be provided to prevent inadvertent motion of the trigger 552 and premature deployment of the suture. In the illustrative example of FIGS. 17-25, the trigger lock includes an arm 572 (FIG. 19) mounted on a pivot 574 for rotation relative to the handle 518 and having a catch 576 spaced from the pivot that engages a slot 578 in the trigger yoke 554. A spring 580 presses on a catch lever 582 and biases the lock 570 into engagement with the trigger 552. Pressing on the catch lever 582 overcomes the spring pressure and rotates the arm 572 so that the catch disengages from the slot and the trigger is free to be rotated by pulling the trigger toward the handle.

Figure 18:
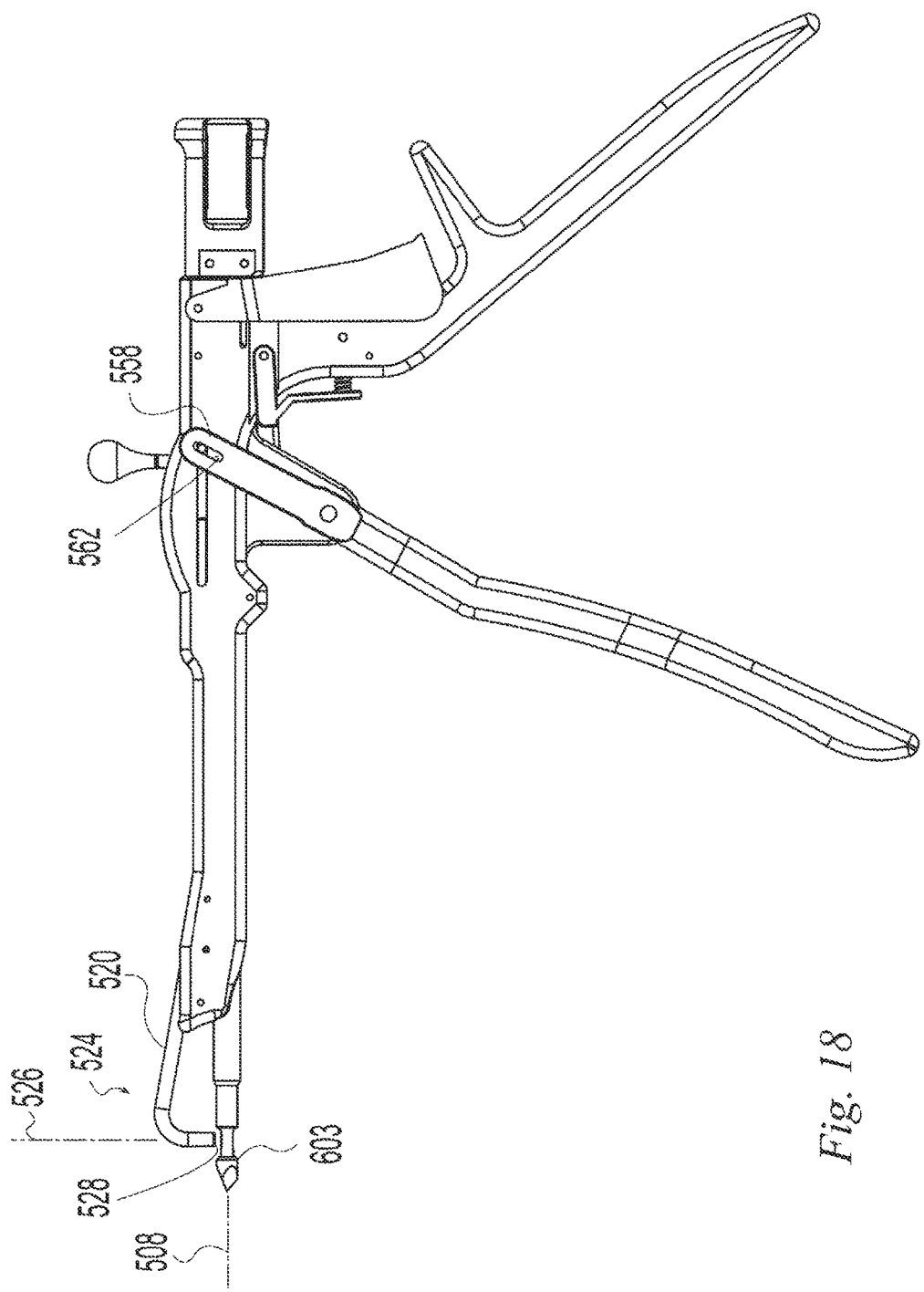
FIG. 18 is a side elevation view of the instrument of FIG. 17.
Figure 19:
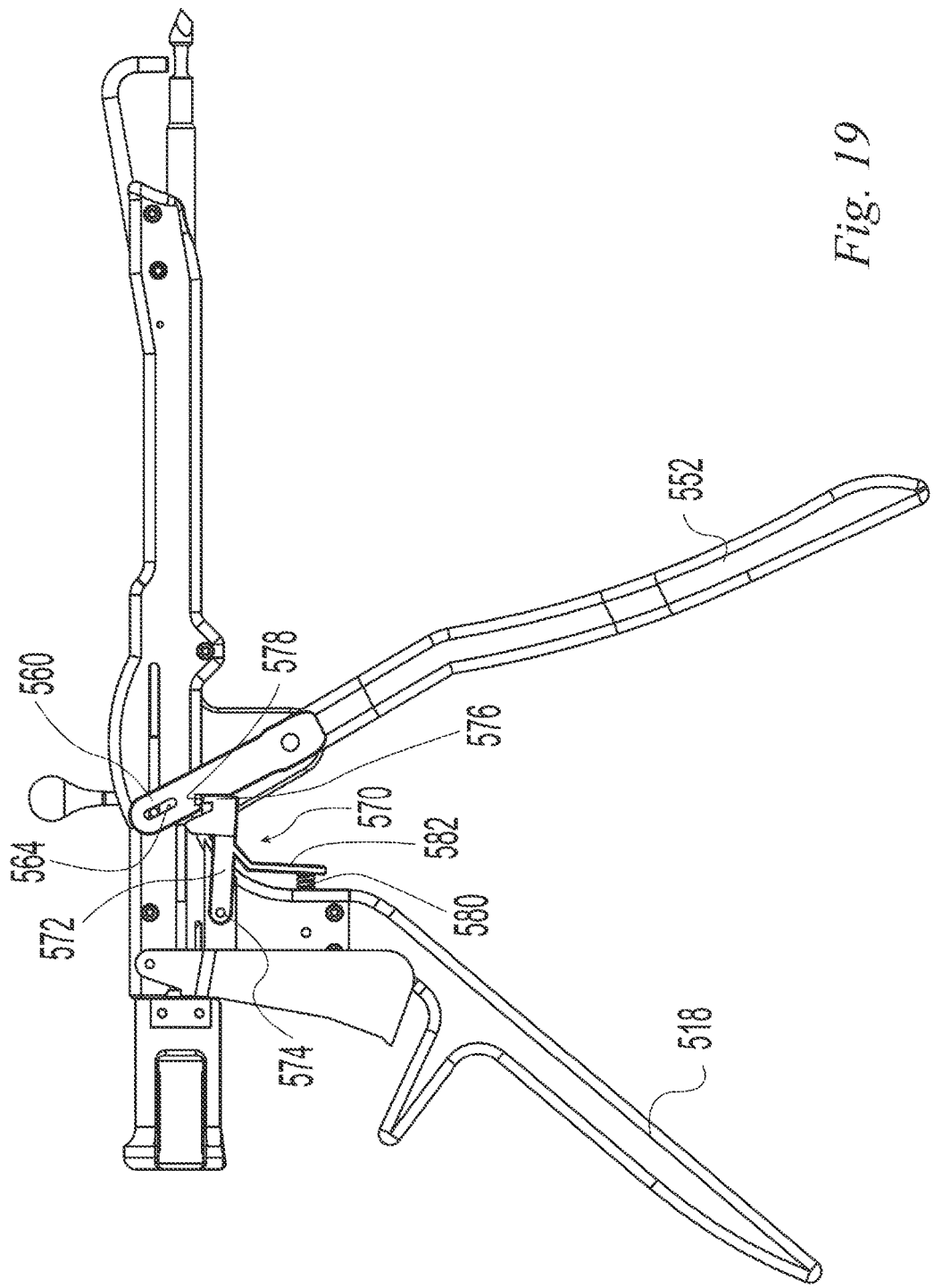
FIG. 19 is a side elevation view of the instrument of FIG. 17, opposite the view of FIG. 17.

The retriever assembly 590 (FIG. 20) includes a retriever sleeve 592 mounted for axial translation within the retriever guide passage 514 along the shaft axis 508. A detent 594 formed in the sleeve 592 is engageable with a spring biased plunger 596 mounted in the handle to give tactile feedback when the sleeve is retracted proximally to a predetermined axial position. The sleeve 592 includes a radial flange 598 at its proximal end. A retriever shaft 600 is mounted for axial translation within the retriever sleeve 592 along the shaft axis 508. The retriever shaft 600 includes a distal end 602 (FIG. 17) defining a sharpened distal tip 604 configured to penetrate bone and forming a shoulder 603 (FIG. 18). In the illustrative example of FIGS. 17-25, the tip 604 has an outer diameter equal to or slightly greater than a reduced diameter portion 605 (FIG. 17) of the distal end of the sleeve 592 such that the reduced diameter portion 605 of the sleeve can follow the tip 604 into a bone tunnel formed by impacting the tip 604 into a bone. A transverse aperture 606 is formed through the retriever shaft near the distal end 602 but proximal to the tip 604. The retriever shaft includes a proximal end 608 (FIG. 20) to which a knob 610 is mounted. Pushing the knob distally along the shaft axis 508 moves the retriever shaft 600 distally within the retriever sleeve 592. Pulling the knob proximally moves the retriever shaft 600 proximally within the retriever sleeve 592. An opening 612 in the distal end of the knob receives the flange 598 of the sleeve 592 in axial translating relationship. A back wall 614 or bottom of the opening 612 abuts the proximal end of the sleeve at the flange 598 and thus defines the distal most axial position of the retriever shaft 600 relative to the sleeve 592 when the knob 610 is pushed distally. Pins 616 mounted through the knob and transverse to the opening 612 abut the distal side of the flange 598 and thus define the proximal most axial position of the retriever shaft 600 relative to the sleeve 592 when the knob 610 is pulled proximally.

A sleeve lock 620 is mounted for rotation to the guide and includes a lip 622 that engages a shoulder 624 on the sleeve 592 to prevent the sleeve from moving proximally from its distal most position in the retriever guide passage 514. A spring 626 biases the sleeve lock 620 into engagement with the sleeve 592. Pressing the sleeve lock 620 overcomes the spring tension and pivots the sleeve lock 620 out of engagement with the sleeve 592 to release the sleeve.

FIGS. 20-25 illustrate the guide 500 in use. Referring to FIG. 20, the knob 610 is pulled proximally to position the retriever sleeve 592 and shaft 600 in their proximal most positions with the plunger 596 engaged with the detent 594 of the sleeve. A portion 532 of a suture 630 is placed in the slot 530 in the tip of the probe 512. A first bone tunnel 650 is formed in a bone 652. In the illustrative example of FIGS. 17-25, a vertical bone tunnel is formed in the humeral head below a torn rotator cuff. The probe 512 is inserted into the first bone tunnel and the angle of the guide 500 is adjusted to aim the shaft axis 508 at a desired entry location for a second bone tunnel. With the probe 512 inserted in the first bone tunnel 650, the guide 500 is indexed relative to the first bone tunnel.

Figure 21:
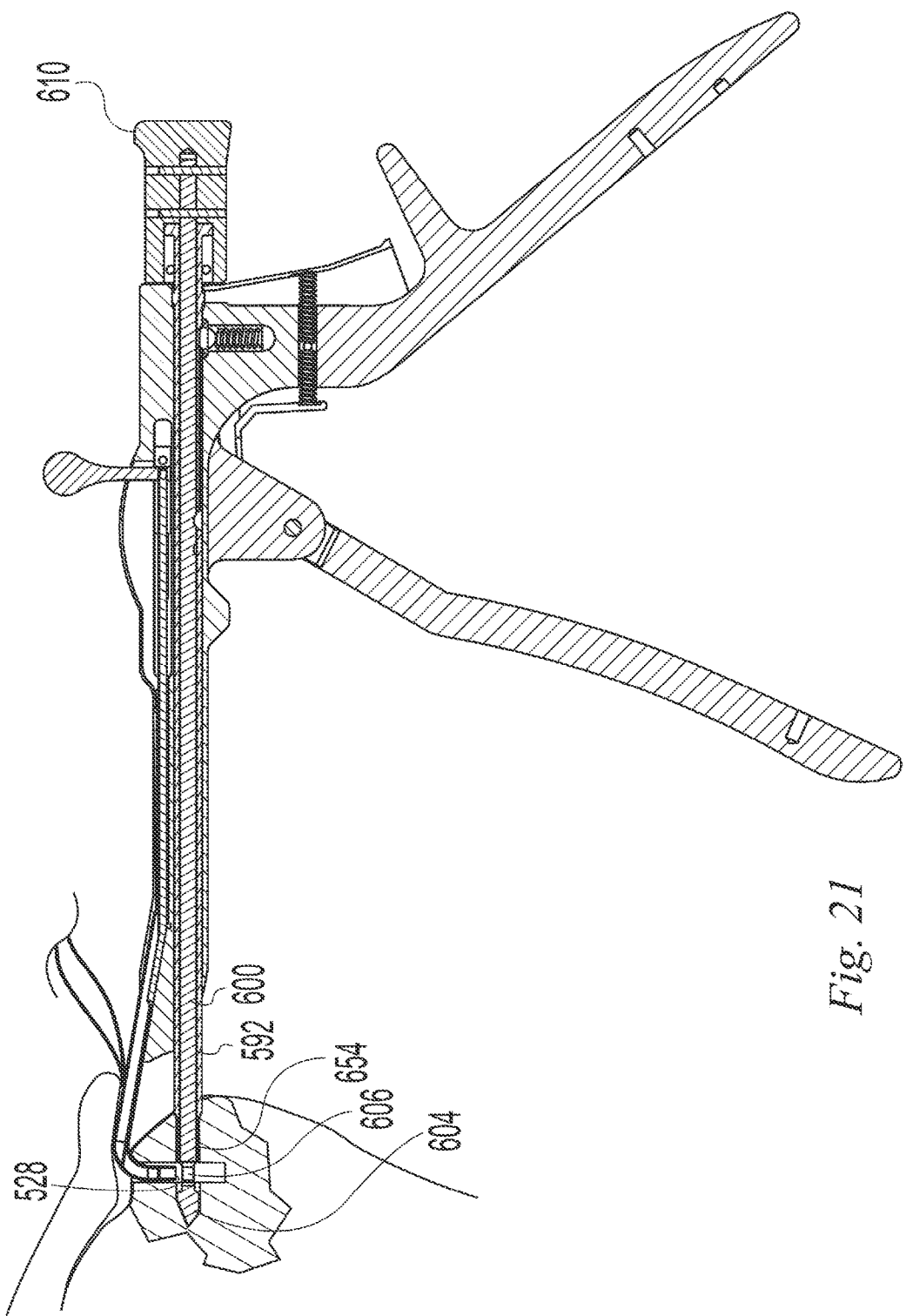

Referring to FIG. 21, the knob 610 is pushed distally until the tip 604 of the retriever shaft 600 is in contact with the bone. The knob is then impacted to drive the retriever shaft 600 and sleeve 592 into the bone and form a second bone tunnel 654. With the retriever shaft 600 and sleeve 592 driven to their proximal most position, the aperture 606 in the retriever shaft 600 is aligned with the exit opening 528 of the probe.

Figure 22:
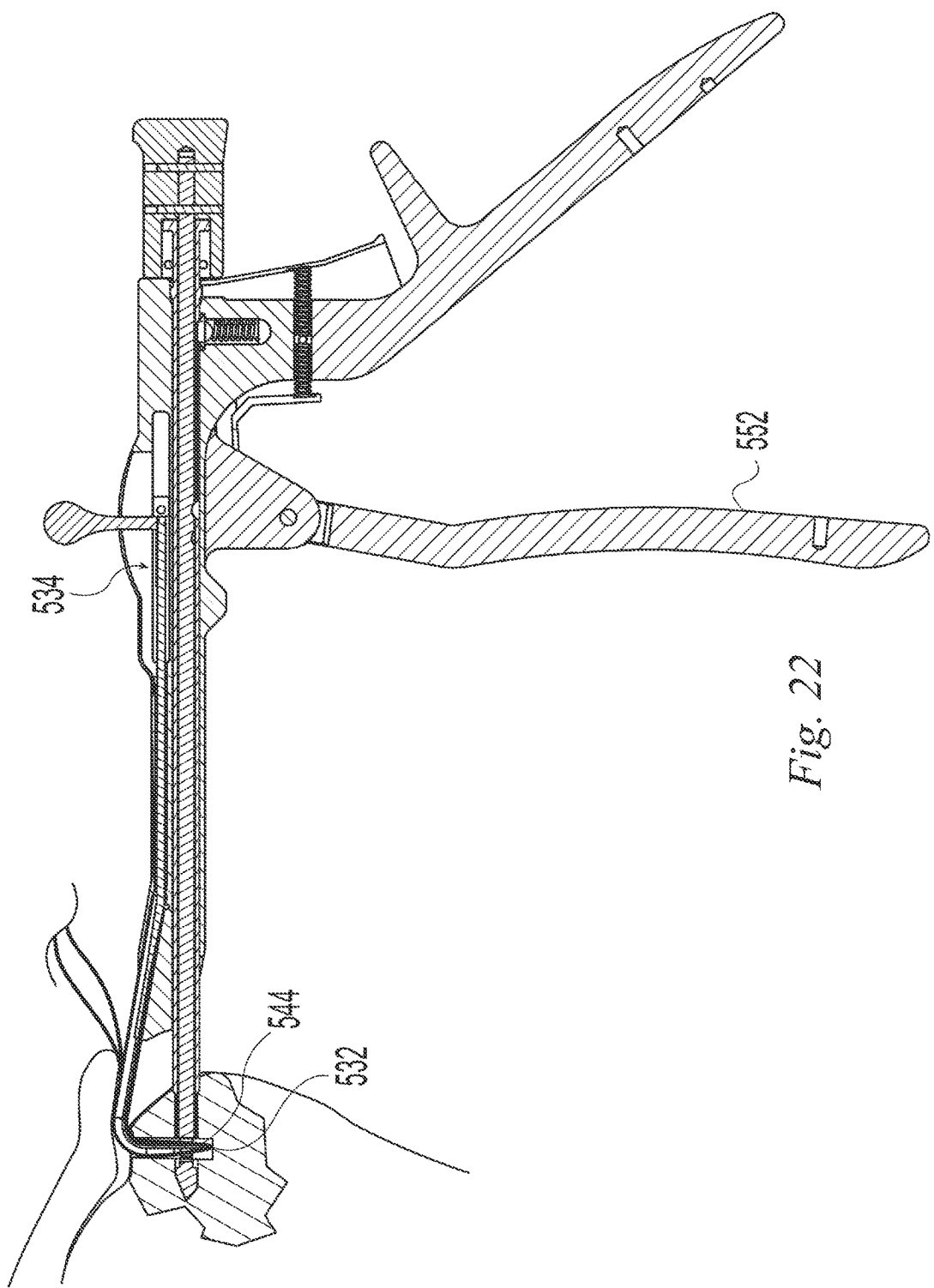

Referring to FIG. 22, the trigger 552 is released and pulled proximally to drive the suture passer assembly 534 distally. The tip 544 of the suture passer shaft 540 urges the suture portion 532 through the aperture 606.

Figure 23:
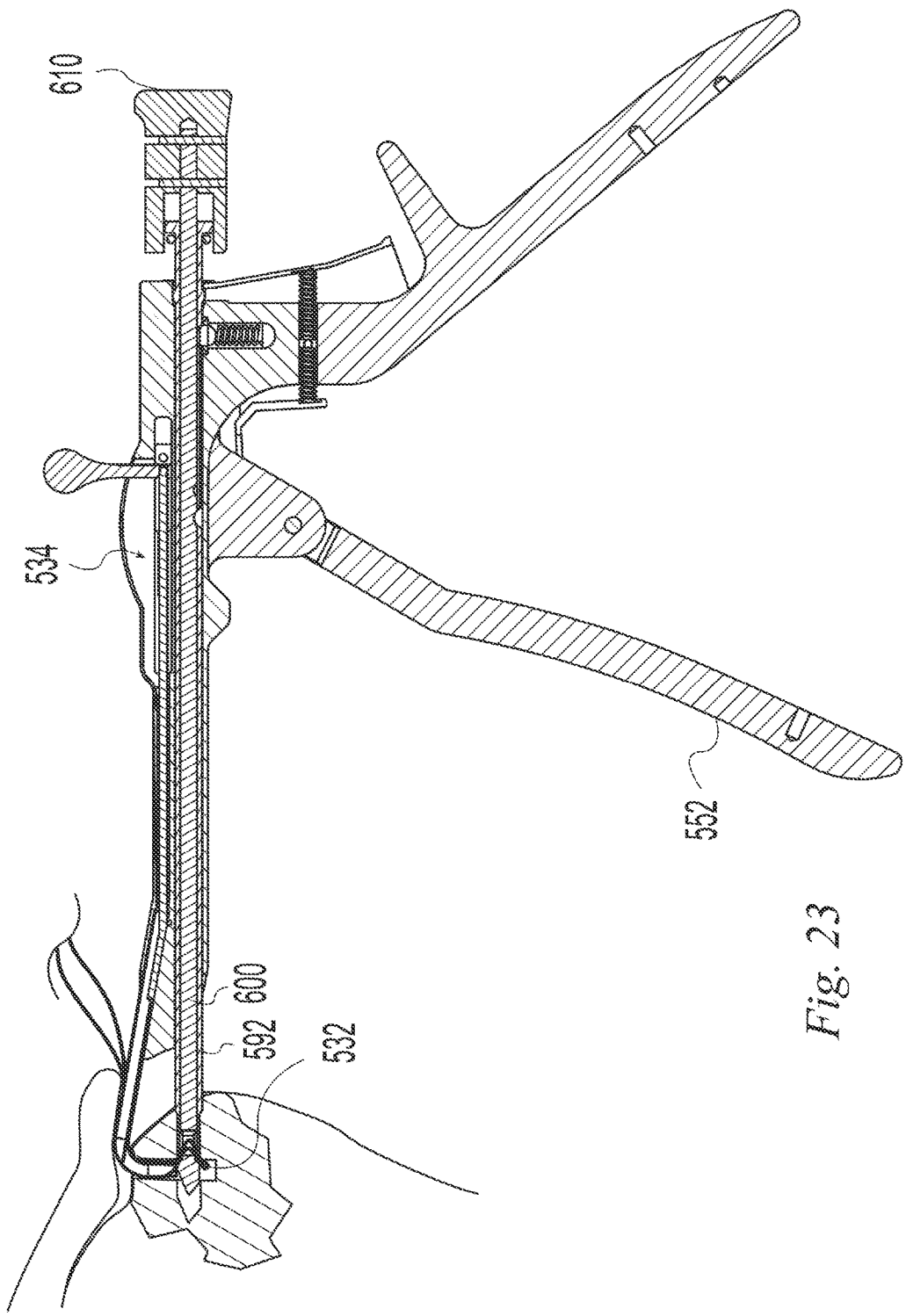

Referring to FIG. 23, the trigger 552 is moved distally to retract the suture passer assembly 534 leaving the suture portion 532 through the aperture 606. The knob 610 is pulled proximally to translate the retriever shaft 600 proximally relative to the sleeve 592 which retracts the aperture 606 into the distal end of the sleeve 592 and traps the suture between the distal end of the sleeve 592 and the shoulder 603 of the tip 604 of the retriever shaft.

Figure 24:
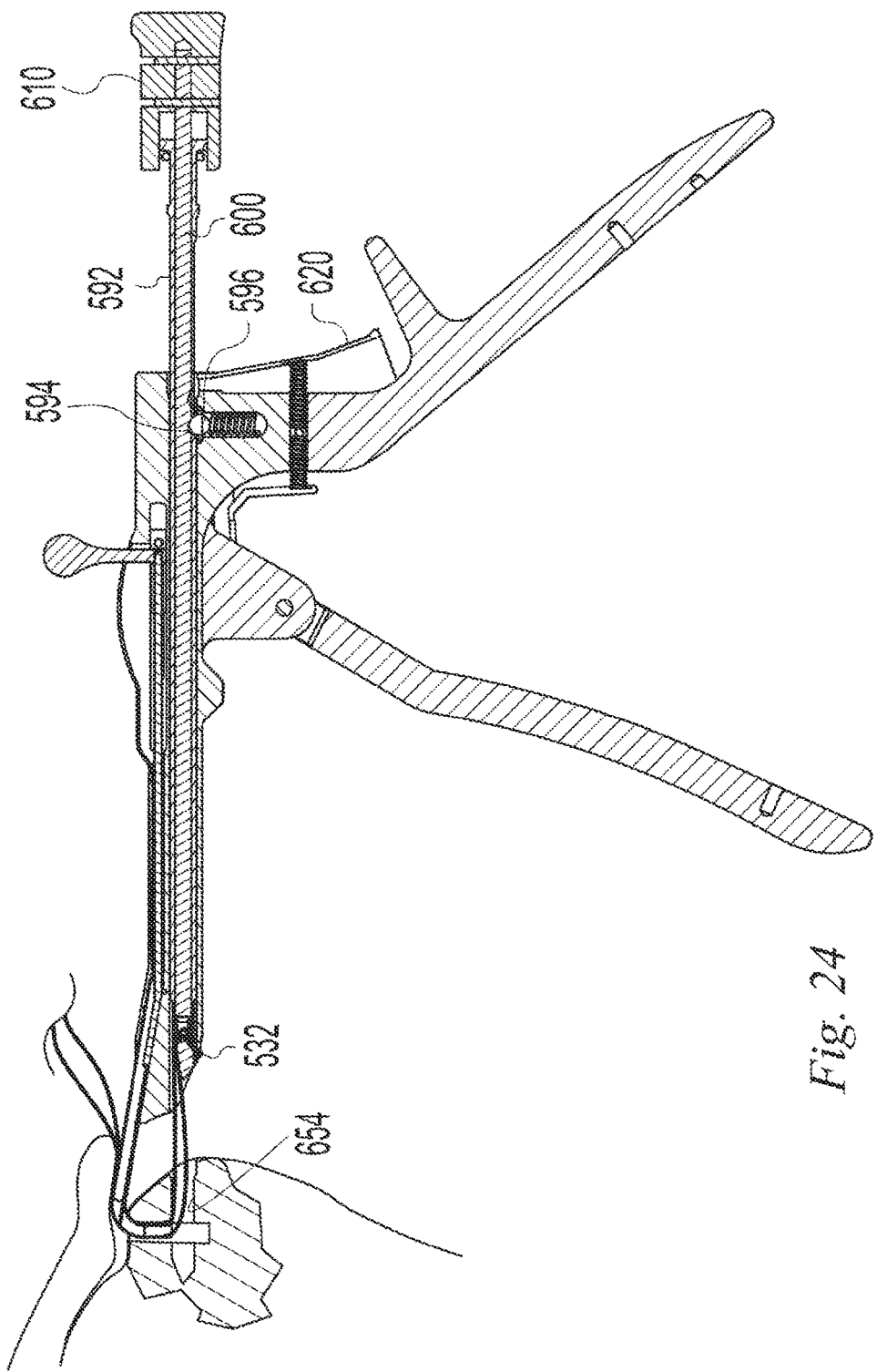

Referring to FIG. 24, the sleeve lock 620 is depressed to release the sleeve 592. The knob 610 is pulled proximally to pull the sleeve 592, retriever shaft 600, and suture portion 532 from the second bone tunnel 654. The knob 610 is pulled until the sleeve detent 594 engages the plunger 596 at which position the distal end of the sleeve 592 and retriever shaft 600 are withdrawn into the retriever guide passage 514 trapping the suture portion 532 within the distal end of the retriever guide passage 514.

Referring to FIG. 25, the probe 512 is extracted from the first bone tunnel 650 and the guide 500 is pulled away from the surgical site to feed the suture 630 through the first and second bone tunnels. The suture 630 may now be used to affix the soft tissue to the bone in a transosseous manner.

Instruments and a method have been described for placing a suture through a bone for a transosseous attachment technique. Aspects of the instruments and techniques may be used in a variety of ways. As an example, the suture punching technique may be used to efficiently place a suture into a bone anytime such a placement is needed and may eliminate the need for a separate drilling step. For example, the punch may be used to punch a suture into a bone after which the punch is removed and a plug is placed in the hole to trap the suture in the bone. For example, as shown in FIGS. 26-28, a suture 750 may be punched into a bone 752 and then a bone dowel 754 tapped in to form a completely tissue based suture-to-bone attachment. FIG. 27 is a cross sectional view. FIG. 24 is a cross sectional view 90 degrees from FIG. 26. FIG. 25 is a top plan view.

Figure 29:
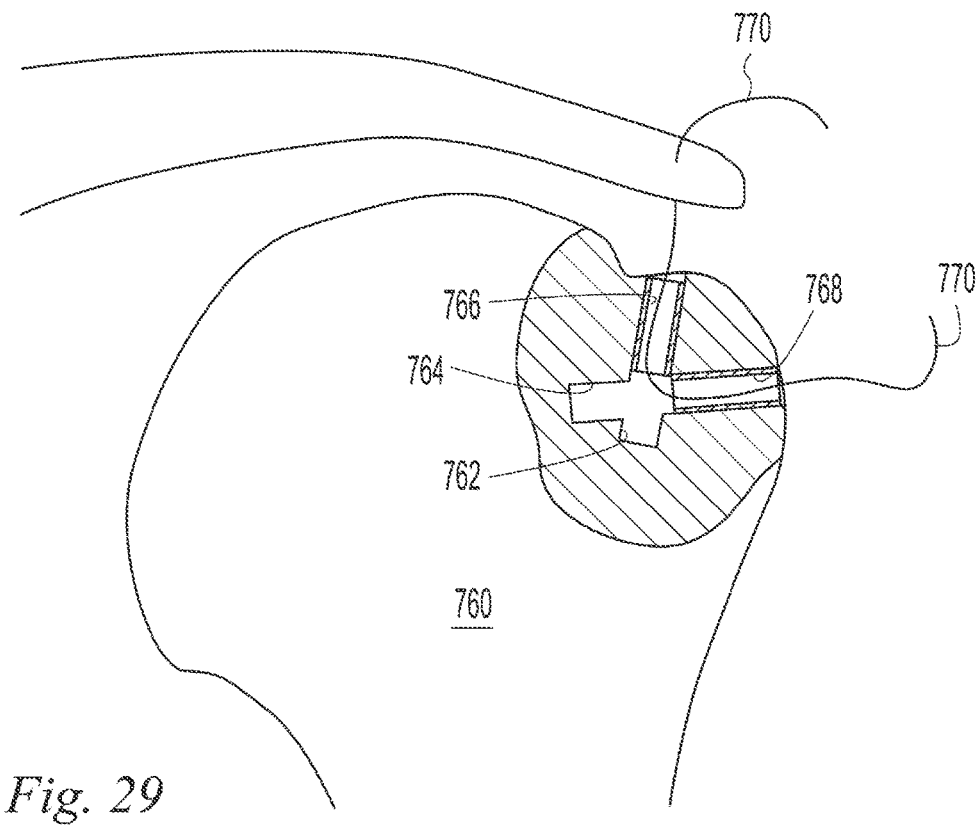
FIG. 29 is a side section view illustrating a method of reinforcing bone tunnels formed with instruments similar to those of FIG. 1.

A bone tunnel may be reinforced by implanting a sleeve in the bone tunnel to prevent a suture from cutting into the bone when it is tensioned. FIG. 29 is a partial cross sectional view of a bone 760 with two intersecting bone tunnels 762, 764 formed such as with one of the previously described guides and techniques. Each tunnel has been reinforced with a sleeve implant 766, 768. Optionally, only one of the tunnels may be reinforced as desired. The sleeves 766, 768 may be inserted manually and a suture 770 threaded manually through them. Alternatively, the sleeves may be inserted simultaneously with the suture punch and/or retriever.

Figure 30:
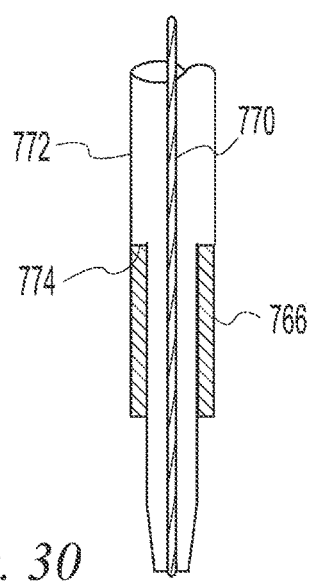
FIGS. 30 and 31 are partial side section views illustrating modifications to instruments of FIG. 1 to allow them to simultaneously form bone tunnels and reinforce the bone tunnels.

FIG. 30 is a partial cross sectional view illustrating a punch shaft 772 having a distal facing shoulder 774 formed on it. A sleeve 766 may be mounted on the shaft 772 abutting the shoulder 774 such that the punch, suture 770, and sleeve 766 are impacted into the bone 760 together. When the punch is withdrawn, the suture 770 and sleeve 766 are left behind with the sleeve 766 lining and reinforcing the bone tunnel 762.

Figure 31:
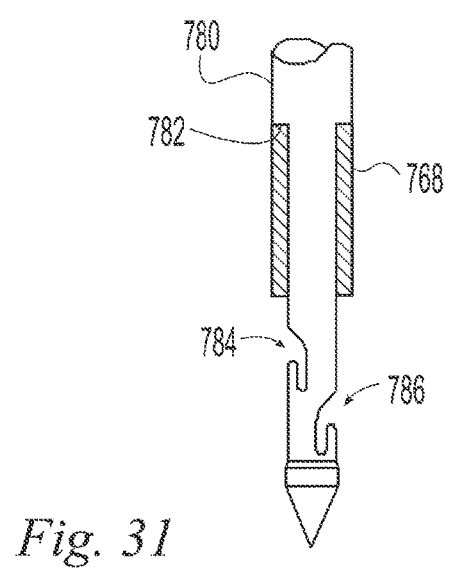

FIG. 31 is a partial cross sectional view illustrating a retriever shaft 780 having a distal facing shoulder 782 formed on it proximal to notches 784, 786. A sleeve 768 may be mounted on the shaft 780 abutting the shoulder 782 such that the retriever and sleeve 768 are impacted into the bone 760 together. When the retriever is withdrawn to retrieve the suture, the sleeve 768 is left behind to line and reinforce the tunnel 764 and the suture is withdrawn through the sleeve 768.

Figure 32:
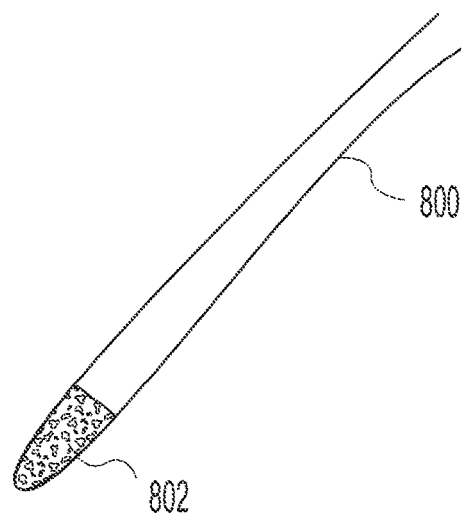
FIG. 32 is a side elevation view of an alternative suture useable with the instruments of FIG. 1.
Figure 33:
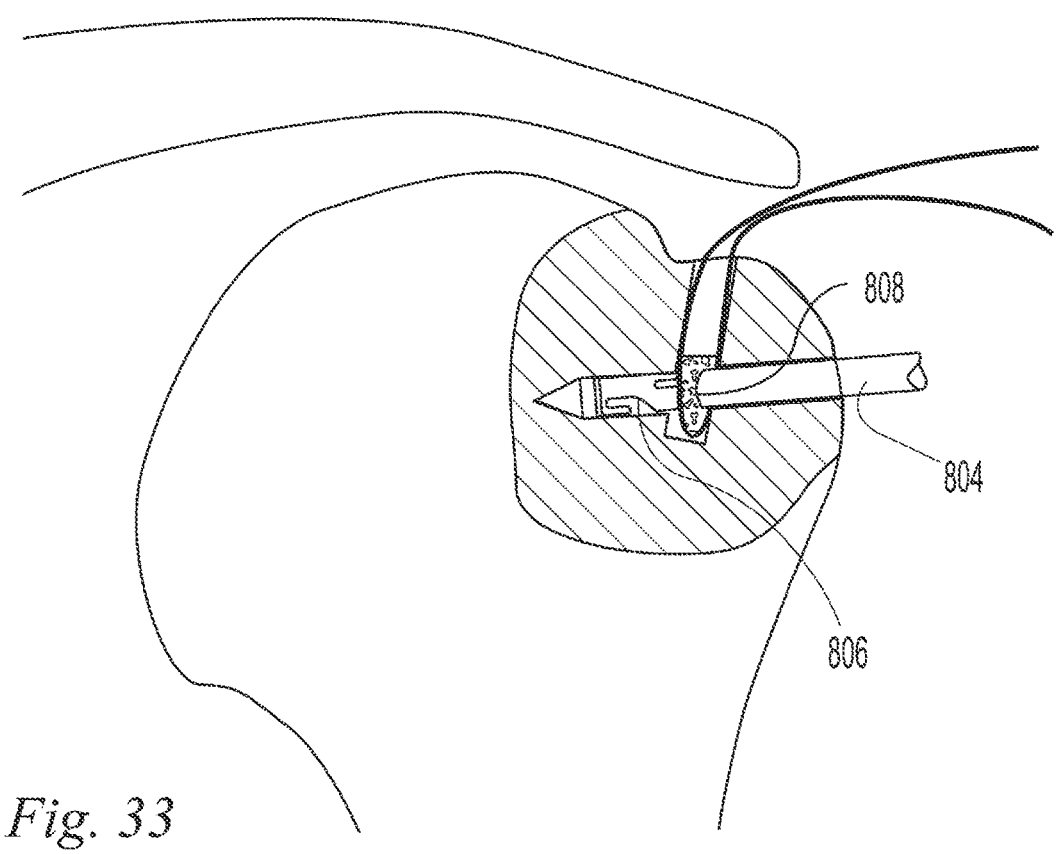
FIG. 33 is a side section view illustrating the use of the suture of FIG. 32.

FIGS. 32 and 33 illustrate an alternative to a plain suture. A suture 800 has an expanded portion 802 that may be placed in the first bone tunnel to improve the efficiency by which the retriever 804 captures the suture. When the retriever 804 is inserted to intersect the first bone tunnel and suture, it passes through the expanded portion 802 of the suture. Upon withdrawal, the notch 806 in the retriever snags on the expanded portion 802 and thereby captures it. The expanded portion has a width dimension greater than the strand thickness of the suture. Because the expanded portion 802 presents a larger target for the retriever than a plain suture, it is more likely that the expanded portion will be captured regardless of which portion of the expanded portion the retriever passes through. As the retriever 804 passes through the expanded portion 802, it creates an opening 808 just large enough for the retriever to pass. As the retriever notch 806 reaches the expanded portion, this opening tends to collapse so that the edge of the opening falls within the notch 806 and is captured upon withdrawal of the retriever. The expanded portion 802 may include a membrane, enlarged braid, knitted fabric, woven fabric, parallel fibers, non-woven fabric, mesh, and/or other suitable portion larger than an individual suture strand. For example, a suture strand may be woven through a mesh, membrane, or fabric so that the material is captured at an intermediate portion of the suture. In another example, a portion of a suture may be unwound and teased apart to create an expanded portion.

While the illustrative examples have shown bone tunnels being formed by punching instruments into the bone, it is also within the scope of the invention to form bone tunnels by drilling, reaming, broaching, and/or any suitable tunnel forming process. The various guide instruments have illustrated different features for indexing the guide to the first bone tunnel in order to guide the formation of a second bone tunnel. The indexing features may include, but are not limited to, a tube, a passage, a slot, and a probe. It is contemplated, and within the scope of the invention, that the various features of the illustrative examples may be interchanged among the illustrative examples.

What is claimed is:

1. A method of placing a suture transosseously through a bone, the method comprising:
    forming a first bone tunnel in the bone;
    positioning a portion of a suture in the first bone tunnel;
    indexing a guide to the first bone tunnel while the suture is in the first bone tunnel;
    guiding a tunnel forming instrument with the guide to form a second bone tunnel transverse to and intersecting the first bone tunnel while the guide is indexed to the first bone tunnel; and
    withdrawing the portion of the suture from the first bone tunnel through the second bone tunnel, wherein the first bone tunnel is formed by impacting a tunnel forming instrument into the bone and wherein the portion of suture is positioned in the first bone tunnel simultaneously with impacting a tunnel forming instrument into the bone to form the first bone tunnel.

2. The method of claim 1 wherein the first bone tunnel is formed into the bone by impacting a bone tunnel punch and the portion of suture is carried by the bone tunnel punch to simultaneously embed the portion of suture in the first bone tunnel as it is formed, the method further comprising at least partially withdrawing the bone tunnel punch prior to forming the second bone tunnel leaving a loop of suture embedded in the first bone tunnel.

3. A method of placing a suture transosseously through a bone, the method comprising:
    forming a first bone tunnel in the bone;
    positioning a portion of a suture in the first bone tunnel;
    indexing a guide to the first bone tunnel while the suture is in the first bone tunnel;
    guiding a tunnel forming instrument with the guide to form a second bone tunnel transverse to and intersecting the first bone tunnel while the guide is indexed to the first bone tunnel; and
    withdrawing the portion of the suture from the first bone tunnel through the second bone tunnel, wherein the step of indexing a guide to the first bone tunnel comprises engaging a portion of the guide with a member inserted in the first bone tunnel, the member being separately inserted into the first bone tunnel prior to engaging the portion of the guide with the member and the member remaining in the first bone tunnel and engaged with the guide while the second bone tunnel is formed.

4. The method of claim 3 wherein the member inserted in the first bone tunnel comprises a first bone tunnel forming instrument used to form the first bone tunnel.

5. The method of claim 4 wherein engaging a portion of the guide with a member inserted in the first bone tunnel comprises coaxially engaging a passage in the guide with the first bone tunnel forming instrument.

6. The method of claim 4 wherein engaging a portion of the guide with a member inserted in the first bone tunnel comprises laterally engaging a slot in the guide with the first bone tunnel forming instrument.

7. A method of placing a suture transosseously through a bone, the method comprising:
    forming a first bone tunnel in the bone;
    positioning a portion of a suture in the first bone tunnel;
    indexing a guide to the first bone tunnel while the suture is in the first bone tunnel;
    guiding a tunnel forming instrument with the guide to form a second bone tunnel transverse to and intersecting the first bone tunnel while the guide is indexed to the first bone tunnel; and
    withdrawing the portion of the suture from the first bone tunnel through the second bone tunnel, wherein the guide includes an indexing probe, the indexing probe being inserted into the first bone tunnel to index the guide to the first bone tunnel, the portion of the suture being delivered to the first bone tunnel from the indexing probe and wherein the indexing probe is hollow and the guide further comprises a suture passer with an end moveable within the indexing probe between a first retracted position and a second extended position in which the suture passer moves the suture into engagement with a suture retriever positioned in the second bone tunnel.

8. The method of claim 7 wherein the suture retriever comprises a retriever shaft having a distal end and a transverse aperture adjacent the distal end, the retriever shaft being mounted coaxially within a retriever sleeve for relative axial translation between a first position in which the transverse aperture is relatively open and able to receive the suture portion and a second position in which the retriever sleeve at least partially covers the transverse aperture to grip the suture, the suture passer passing the portion of suture through the transverse aperture of the suture retriever.

9. A method of placing a suture transosseously through a bone, the method comprising:
    forming a first bone tunnel in the bone;
    positioning a portion of a suture in the first bone tunnel;
    indexing a guide to the first bone tunnel while the suture is in the first bone tunnel;
    guiding a tunnel forming instrument with the guide to form a second bone tunnel transverse to and intersecting the first bone tunnel while the guide is indexed to the first bone tunnel;
    withdrawing the portion of the suture from the first bone tunnel through the second bone tunnel;
    reinforcing at least one of the first and second bone tunnels by simultaneously inserting a reinforcing member into the one of the first and second bone tunnels as the one of the first and second bone tunnels is formed to create a reinforced bone tunnel, the reinforcing member remaining in the reinforced bone tunnel after a tunnel forming instrument is removed from the reinforced bone tunnel and after the suture is withdrawn through the second bone tunnel; and
    leaving the suture and reinforcing member in the reinforced bone tunnel as implants after completing a surgical procedure.

10. The method of claim 9 wherein the reinforcing member comprises a sleeve and the tunnel forming instrument comprises a punch coaxially receiving the sleeve so that the sleeve is punched into the bone with the punch as the reinforced tunnel is formed and remains in the bone upon withdrawal of the punch.

11. A method of placing a suture transosseously through a bone, the method comprising:
    forming a first bone tunnel in the bone;
    inserting a member extending from a guide into the first bone tunnel to index the guide to the first bone tunnel;
    while the member is inserted into the first bone tunnel, guiding a tunnel forming instrument with the guide to form a second bone tunnel transverse to and intersecting the first bone tunnel;
    after forming the second bone tunnel and while the member is inserted into the first bone tunnel and without removing the tunnel forming instrument from the second bone tunnel, advancing a portion of a suture in the first bone tunnel so that it engages the tunnel forming instrument; and
    withdrawing the portion of the suture through the second bone tunnel with the tunnel forming instrument.

12. The method of claim 11 wherein the guide includes an indexing probe, the step of indexing the guide comprising inserting the indexing probe into the first bone tunnel and the step of advancing a portion of a suture comprising advancing the portion of suture from the indexing probe.

13. The method of claim 12 wherein the indexing probe is hollow and the guide further comprises a suture passer with an end moveable within the indexing probe between a first retracted position and a second extended position the method further comprising moving the suture passer from the first retracted position to the second extended position to advance the portion of a suture in the first bone tunnel and engage the suture with the tunnel forming instrument while the tunnel forming instrument is positioned in the second bone tunnel.

14. The method of claim 13 wherein the tunnel forming instrument comprises a retriever shaft having a distal end and a transverse aperture adjacent the distal end, the retriever shaft being mounted coaxially within a retriever sleeve for relative axial translation, the method further comprising translating the retriever shaft relative to the retriever sleeve to trap the portion of suture in the transverse aperture of the tunnel forming instrument.

15. The method of claim 11 wherein the step of guiding a tunnel forming instrument comprises punching the tunnel forming instrument through the bone to form the second bone tunnel.

* * * * *